United States Patent
Taub

(10) Patent No.: US 8,734,344 B2
(45) Date of Patent: May 27, 2014

(54) ON-BODY MEDICAL DEVICE SECUREMENT

(75) Inventor: Marc B. Taub, Mountain View, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 269 days.

(21) Appl. No.: 13/118,441

(22) Filed: May 29, 2011

(65) Prior Publication Data

US 2011/0288386 A1 Nov. 24, 2011

Related U.S. Application Data

(63) Continuation of application No. 12/610,237, filed on Oct. 30, 2009, now Pat. No. 7,951,080, which is a continuation of application No. 11/344,434, filed on Jan. 30, 2006, now Pat. No. 7,736,310.

(51) Int. Cl.
*A61B 5/00* (2006.01)

(52) U.S. Cl.
USPC .......................................... 600/309

(58) Field of Classification Search
USPC .......................................... 600/309; 602/903
See application file for complete search history.

(56) References Cited

U.S. PATENT DOCUMENTS

| | | | |
|---|---|---|---|
| 3,581,062 A | 5/1971 | Aston | |
| 3,926,760 A | 12/1975 | Allen et al. | |
| 3,949,388 A | 4/1976 | Fuller | |
| 4,036,749 A | 7/1977 | Anderson | |
| 4,055,175 A | 10/1977 | Clemens et al. | |
| 4,129,128 A | 12/1978 | McFarlane | |
| 4,245,634 A | 1/1981 | Albisser et al. | |
| 4,327,725 A | 5/1982 | Cortese et al. | |
| 4,344,438 A | 8/1982 | Schultz | |
| 4,349,728 A | 9/1982 | Phillips et al. | |
| 4,425,920 A | 1/1984 | Bourland et al. | |
| 4,478,976 A | 10/1984 | Goertz et al. | |
| 4,494,950 A | 1/1985 | Fischell | |
| 4,509,531 A | 4/1985 | Ward | |
| 4,527,240 A | 7/1985 | Kvitash | |
| 4,538,616 A | 9/1985 | Rogoff | |
| 4,619,793 A | 10/1986 | Lee | |
| 4,671,288 A | 6/1987 | Gough | |
| 4,703,756 A | 11/1987 | Gough et al. | |
| 4,731,726 A | 3/1988 | Allen, III | |

(Continued)

FOREIGN PATENT DOCUMENTS

| | | |
|---|---|---|
| DE | 4401400 | 7/1995 |
| EP | 0098592 | 1/1984 |

(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner* — Michael D'Angelo
*Assistant Examiner* — Christian Jang
(74) *Attorney, Agent, or Firm* — Jackson & Co., LLP

(57) ABSTRACT

Devices and methods for maintaining a medical device on-body are provided. Embodiments include medical device securement systems having first and second on-body securement elements. Also provided are systems and kits for use maintaining a medical device on-body.

15 Claims, 18 Drawing Sheets

(56) References Cited

U.S. PATENT DOCUMENTS

| | | |
|---|---|---|
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,854,322 A | 8/1989 | Ash et al. |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,082,550 A | 1/1992 | Rishpon et al. |
| 5,106,365 A | 4/1992 | Hernandez |
| 5,122,925 A | 6/1992 | Inpyn |
| 5,165,407 A | 11/1992 | Wilson et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,390,671 A | 2/1995 | Lord et al. |
| 5,391,250 A | 2/1995 | Cheney, II et al. |
| 5,394,877 A | 3/1995 | Orr et al. |
| 5,402,780 A | 4/1995 | Faasse, Jr. |
| 5,408,999 A | 4/1995 | Singh et al. |
| 5,411,647 A | 5/1995 | Johnson et al. |
| 5,431,160 A | 7/1995 | Wilkins |
| 5,431,921 A | 7/1995 | Thombre |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,653,239 A | 8/1997 | Pompei et al. |
| 5,665,222 A | 9/1997 | Heller et al. |
| 5,711,001 A | 1/1998 | Bussan et al. |
| 5,711,861 A | 1/1998 | Ward et al. |
| 5,735,285 A | 4/1998 | Albert et al. |
| 5,772,586 A | 6/1998 | Heinonen et al. |
| 5,791,344 A | 8/1998 | Schulman et al. |
| 5,807,375 A | 9/1998 | Gross et al. |
| 5,875,186 A | 2/1999 | Belanger et al. |
| 5,899,855 A | 5/1999 | Brown |
| 5,925,021 A | 7/1999 | Castellano et al. |
| 5,942,979 A | 8/1999 | Luppino |
| 5,951,521 A | 9/1999 | Mastrototaro et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,987,353 A | 11/1999 | Khatchatrian et al. |
| 5,995,860 A | 11/1999 | Sun et al. |
| 6,001,067 A | 12/1999 | Shults et al. |
| 6,004,278 A | 12/1999 | Botich et al. |
| 6,022,315 A | 2/2000 | Iliff |
| 6,024,699 A | 2/2000 | Surwit et al. |
| 6,049,727 A | 4/2000 | Crothall |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,129,823 A | 10/2000 | Hughes et al. |
| 6,134,461 A | 10/2000 | Say et al. |
| 6,141,573 A | 10/2000 | Kurnik et al. |
| 6,159,147 A | 12/2000 | Lichter et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,348,640 B1 | 2/2002 | Navot et al. |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,478,736 B1 | 11/2002 | Mault |
| 6,484,045 B1 | 11/2002 | Holker et al. |
| 6,484,046 B1 | 11/2002 | Say et al. |
| 6,514,718 B2 | 2/2003 | Heller et al. |
| 6,551,494 B1 | 4/2003 | Heller et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |

(56) References Cited

U.S. PATENT DOCUMENTS

| | | |
|---|---|---|
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,837,858 B2 | 1/2005 | Cunningham et al. |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,024,245 B2 | 4/2006 | Lebel et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,226,978 B2 | 6/2007 | Tapsak et al. |
| 7,276,029 B2 | 10/2007 | Goode, Jr. et al. |
| 7,278,983 B2 | 10/2007 | Ireland et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,329,239 B2 | 2/2008 | Safabash et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,424,318 B2 | 9/2008 | Brister et al. |
| 7,429,258 B2 | 9/2008 | Angel et al. |
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,697,967 B2 | 4/2010 | Stafford |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |
| 7,736,310 B2 | 6/2010 | Taub |
| 7,736,344 B2 | 6/2010 | Moberg et al. |
| 7,763,042 B2 | 7/2010 | Iio et al. |
| 7,822,454 B1 | 10/2010 | Alden et al. |
| 7,914,460 B2 | 3/2011 | Melker et al. |
| 8,010,174 B2 | 8/2011 | Goode et al. |
| 2001/0020124 A1* | 9/2001 | Tamada ........................ 600/347 |
| 2001/0037060 A1 | 11/2001 | Thompson et al. |
| 2001/0047604 A1* | 12/2001 | Valiulis ..................... 40/661.03 |
| 2002/0019022 A1 | 2/2002 | Dunn et al. |
| 2002/0042090 A1 | 4/2002 | Heller et al. |
| 2002/0103499 A1 | 8/2002 | Perez et al. |
| 2002/0106709 A1 | 8/2002 | Potts et al. |
| 2002/0111832 A1 | 8/2002 | Judge |
| 2002/0128594 A1 | 9/2002 | Das et al. |
| 2002/0133107 A1* | 9/2002 | Darcey ............................. 602/8 |
| 2002/0161288 A1 | 10/2002 | Shin et al. |
| 2002/0188748 A1 | 12/2002 | Blackwell et al. |
| 2003/0021729 A1 | 1/2003 | Moller et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0065308 A1 | 4/2003 | Lebel et al. |
| 2003/0134347 A1 | 7/2003 | Heller et al. |
| 2003/0163351 A1 | 8/2003 | Brown |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0208113 A1 | 11/2003 | Mault et al. |
| 2003/0212379 A1 | 11/2003 | Bylund et al. |
| 2003/0217966 A1 | 11/2003 | Tapsak et al. |
| 2004/0010207 A1 | 1/2004 | Flaherty et al. |
| 2004/0011671 A1 | 1/2004 | Shults et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0060818 A1 | 4/2004 | Feldman et al. |
| 2004/0064068 A1 | 4/2004 | DeNuzzio et al. |
| 2004/0078215 A1 | 4/2004 | Dahlin et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0199059 A1 | 10/2004 | Brauker et al. |
| 2004/0204687 A1 | 10/2004 | Mogensen et al. |

(56) References Cited

U.S. PATENT DOCUMENTS

| | | |
|---|---|---|
| 2004/0225338 A1 | 11/2004 | Lebel et al. |
| 2004/0236200 A1 | 11/2004 | Say et al. |
| 2004/0254433 A1 | 12/2004 | Bandis et al. |
| 2004/0254434 A1 | 12/2004 | Goodnow et al. |
| 2004/0267300 A1 | 12/2004 | Mace |
| 2005/0003470 A1 | 1/2005 | Nelson et al. |
| 2005/0004494 A1 | 1/2005 | Perez et al. |
| 2005/0010269 A1 | 1/2005 | Lebel et al. |
| 2005/0027177 A1 | 2/2005 | Shin et al. |
| 2005/0031689 A1 | 2/2005 | Shults et al. |
| 2005/0038680 A1 | 2/2005 | McMahon |
| 2005/0043598 A1 | 2/2005 | Goode, Jr. et al. |
| 2005/0090607 A1 | 4/2005 | Tapsak et al. |
| 2005/0096511 A1 | 5/2005 | Fox et al. |
| 2005/0112169 A1 | 5/2005 | Brauker et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0137530 A1 | 6/2005 | Campbell et al. |
| 2005/0143635 A1 | 6/2005 | Kamath et al. |
| 2005/0176136 A1 | 8/2005 | Burd et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0277164 A1 | 12/2005 | Drucker et al. |
| 2005/0287620 A1 | 12/2005 | Heller et al. |
| 2006/0001538 A1 | 1/2006 | Kraft et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0079740 A1 | 4/2006 | Silver et al. |
| 2006/0166629 A1 | 7/2006 | Reggiardo |
| 2006/0173406 A1 | 8/2006 | Hayes et al. |
| 2006/0173444 A1 | 8/2006 | Choy et al. |
| 2006/0189863 A1 | 8/2006 | Peyser et al. |
| 2006/0222566 A1 | 10/2006 | Brauker et al. |
| 2006/0226985 A1 | 10/2006 | Goodnow et al. |
| 2006/0247508 A1 | 11/2006 | Fennell |
| 2006/0272652 A1 | 12/2006 | Stocker et al. |
| 2007/0010950 A1 | 1/2007 | Abensour et al. |
| 2007/0016381 A1 | 1/2007 | Kamath et al. |
| 2007/0027381 A1 | 2/2007 | Stafford |
| 2007/0060814 A1 | 3/2007 | Stafford |
| 2007/0073129 A1* | 3/2007 | Shah et al. ............. 600/365 |
| 2007/0078320 A1 | 4/2007 | Stafford |
| 2007/0078321 A1 | 4/2007 | Mazza et al. |
| 2007/0078322 A1 | 4/2007 | Stafford |
| 2007/0093786 A1 | 4/2007 | Goldsmith et al. |
| 2007/0106135 A1 | 5/2007 | Sloan et al. |
| 2007/0149875 A1 | 6/2007 | Ouyang et al. |
| 2007/0163880 A1 | 7/2007 | Woo et al. |
| 2007/0173706 A1 | 7/2007 | Neinast et al. |
| 2007/0203407 A1 | 8/2007 | Hoss et al. |
| 2007/0203539 A1 | 8/2007 | Stone et al. |
| 2007/0203966 A1 | 8/2007 | Brauker et al. |
| 2007/0228071 A1 | 10/2007 | Kamen et al. |
| 2007/0231846 A1 | 10/2007 | Cosentino et al. |
| 2007/0235331 A1 | 10/2007 | Simpson et al. |
| 2007/0249922 A1 | 10/2007 | Peyser et al. |
| 2008/0004904 A1 | 1/2008 | Tran |
| 2008/0009692 A1 | 1/2008 | Stafford |
| 2008/0021666 A1 | 1/2008 | Goode, Jr. et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0108942 A1 | 5/2008 | Brister et al. |
| 2008/0125636 A1 | 5/2008 | Ward et al. |
| 2008/0127052 A1 | 5/2008 | Rostoker |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262469 A1 | 10/2008 | Brister et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0088614 A1 | 4/2009 | Taub |
| 2009/0088787 A1 | 4/2009 | Koike et al. |
| 2009/0099436 A1 | 4/2009 | Brister et al. |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |

(56) References Cited

U.S. PATENT DOCUMENTS

| | | |
|---|---|---|
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0113897 A1 | 5/2010 | Brenneman et al. |
| 2010/0119693 A1 | 5/2010 | Tapsak et al. |
| 2010/0121169 A1 | 5/2010 | Petisce et al. |
| 2010/0145172 A1 | 6/2010 | Petisce et al. |
| 2010/0146300 A1 | 6/2010 | Brown |
| 2010/0152554 A1 | 6/2010 | Steine et al. |
| 2010/0160760 A1 | 6/2010 | Shults et al. |
| 2010/0161269 A1 | 6/2010 | Kamath et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168545 A1 | 7/2010 | Kamath et al. |
| 2010/0168546 A1 | 7/2010 | Kamath et al. |
| 2010/0168657 A1 | 7/2010 | Kamath et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0179399 A1 | 7/2010 | Goode et al. |
| 2010/0179400 A1 | 7/2010 | Brauker et al. |
| 2010/0179401 A1 | 7/2010 | Rasdal et al. |
| 2010/0179402 A1 | 7/2010 | Goode et al. |
| 2010/0179404 A1 | 7/2010 | Kamath et al. |
| 2010/0179405 A1 | 7/2010 | Goode et al. |
| 2010/0179407 A1 | 7/2010 | Goode et al. |
| 2010/0179408 A1 | 7/2010 | Kamath et al. |
| 2010/0179409 A1 | 7/2010 | Kamath et al. |
| 2010/0185065 A1 | 7/2010 | Goode et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode et al. |
| 2010/0185073 A1 | 7/2010 | Goode et al. |
| 2010/0185074 A1 | 7/2010 | Goode et al. |
| 2010/0185075 A1 | 7/2010 | Brister et al. |
| 2010/0191082 A1 | 7/2010 | Brister et al. |
| 2010/0198035 A1 | 8/2010 | Kamath et al. |
| 2010/0198036 A1 | 8/2010 | Kamath et al. |
| 2010/0198142 A1 | 8/2010 | Sloan et al. |
| 2010/0217105 A1 | 8/2010 | Yodfat et al. |
| 2010/0262201 A1 | 10/2010 | He et al. |
| 2010/0331642 A1 | 12/2010 | Bruce et al. |
| 2011/0040256 A1 | 2/2011 | Bobroff et al. |
| 2011/0178461 A1 | 7/2011 | Chong et al. |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| WO | WO-96/25089 | 8/1996 |
| WO | WO-96/35370 | 11/1996 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-03/085372 | 10/2003 |
| WO | WO-2004/061420 | 7/2004 |
| WO | WO-2005/041766 | 5/2005 |
| WO | WO-2005/089103 | 9/2005 |
| WO | WO-2005/119524 | 12/2005 |
| WO | WO-2006/024671 | 3/2006 |
| WO | WO-2006/079114 | 7/2006 |
| WO | WO-2006/086423 | 8/2006 |
| WO | WO-2006/118947 | 11/2006 |
| WO | WO-2008/001366 | 1/2008 |
| WO | WO-2008/086541 | 7/2008 |
| WO | WO-2010/077329 | 7/2010 |

OTHER PUBLICATIONS

Bennion, N., et al., "Alternate Site Glucose Testing: A Crossover Design", *Diabetes Technology & Therapeutics*, vol. 4, No. 1, 2002, pp. 25-33.

(56) References Cited

OTHER PUBLICATIONS

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems, Chapter 15*, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring, Chapter 4*, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

U.S. Appl. No. 11/344,434, Advisory Action mailed Jul. 31, 2009.
U.S. Appl. No. 11/344,434, Notice of Allowance mailed Mar. 2, 2010.
U.S. Appl. No. 11/344,434, Office Action mailed Apr. 30, 2009.
U.S. Appl. No. 11/344,434, Office Action mailed Nov. 3, 2008.
U.S. Appl. No. 11/344,434, Office Action mailed Oct. 29, 2009.
U.S. Appl. No. 12/610,237, Notice of Allowance mailed Apr. 5, 2011.
U.S. Appl. No. 12/610,237, Office Action mailed Mar. 18, 2011.
U.S. Appl. No. 12/610,237, Office Action mailed Oct. 8, 2010.

(56) References Cited

OTHER PUBLICATIONS

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Jovanovic, L., "The Role of Continuous Glucose Monitoring in Gestational Diabetes Mellitus", *Diabetes Technology & Therapeutics*, vol. 2, Sup. 1, 2000, pp. S67-S71.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.

Mougiakakou, et al., "A Real Time Simulation Model of Glucose-Insulin Metabolism for Type 1 Diabetes Patients", *Proceedings of the 2005 IEEE*, 2005, pp. 298-301.

Parker, R., et al., "Robust H∞ Glucose Control in Diabetes Using a Physiological Model", *AIChE Journal*, vol. 46, No. 12, 2000, pp. 2537-2549.

\* cited by examiner

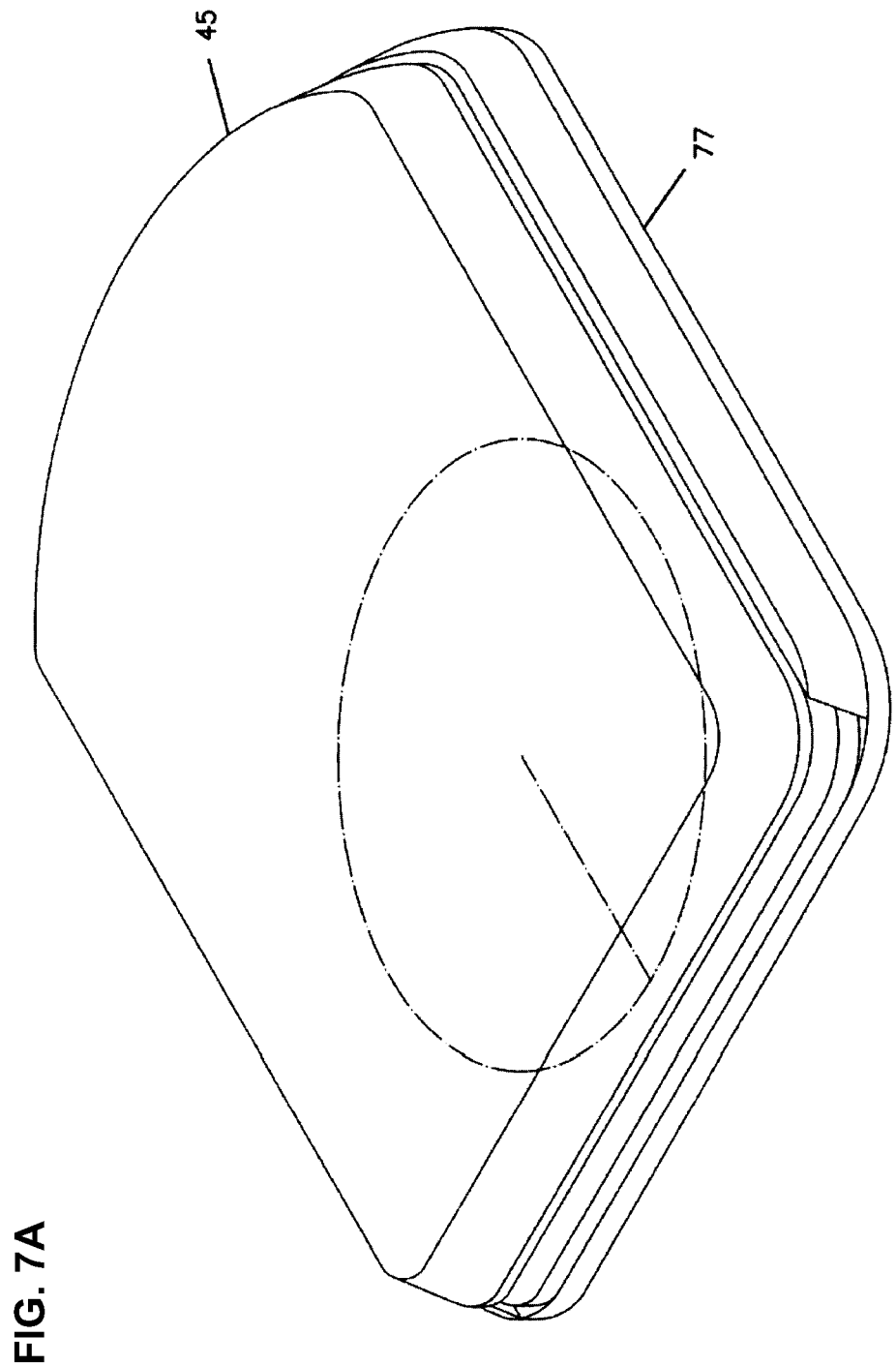

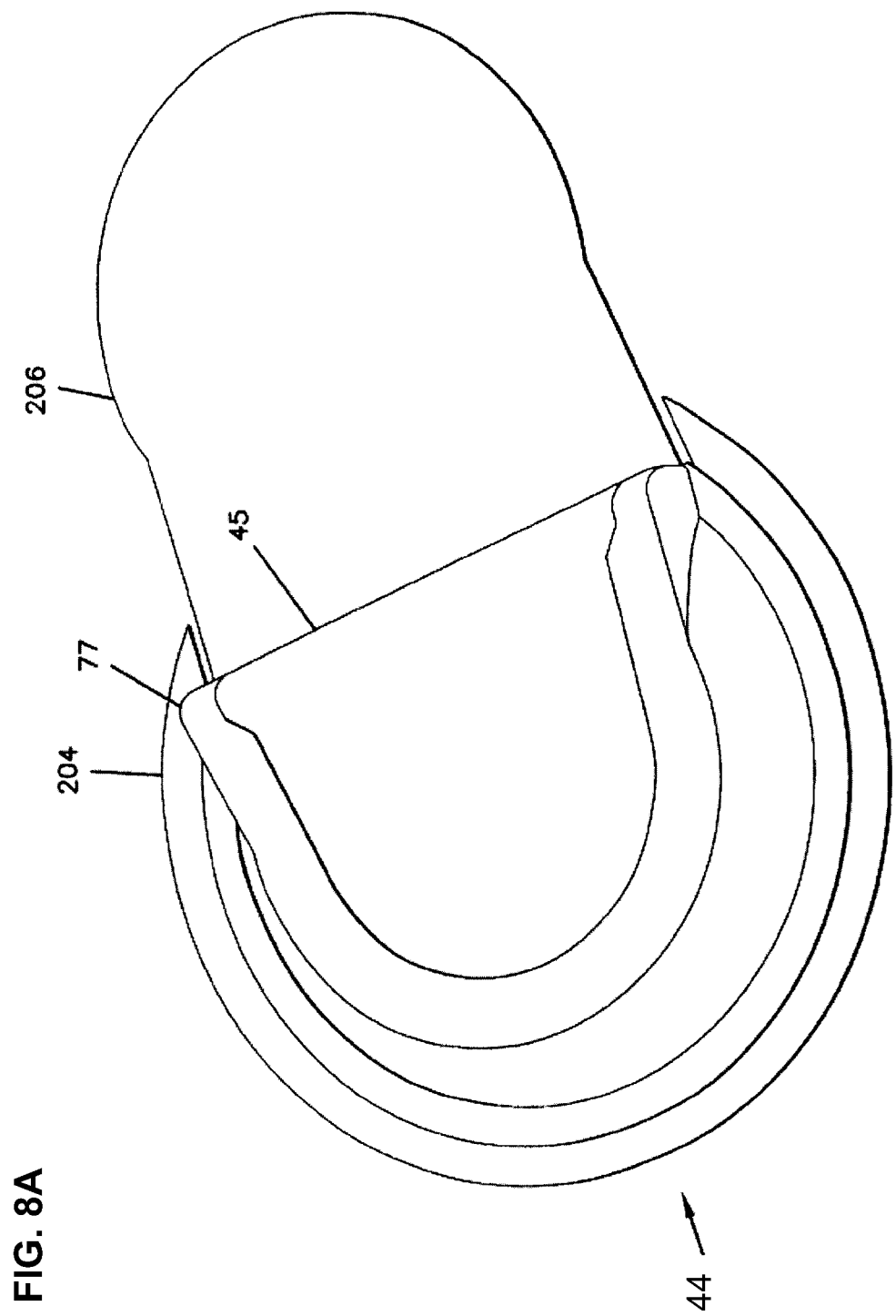

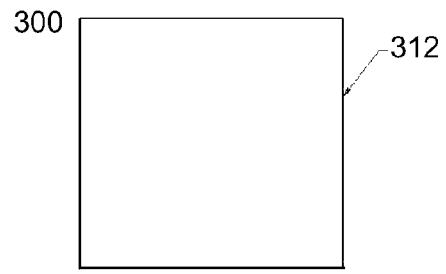
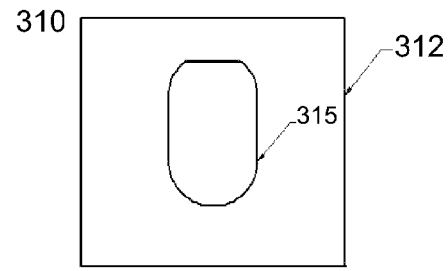
FIG. 9A      FIG. 9B
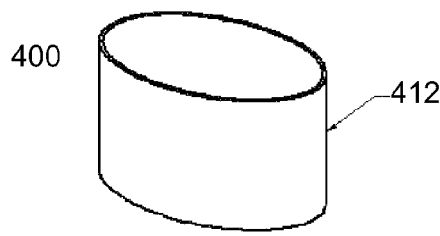
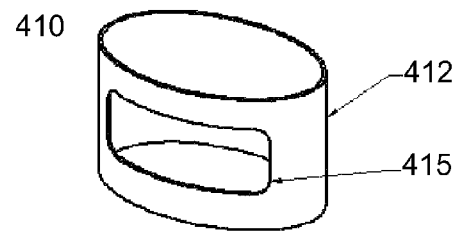
FIG. 10A     FIG. 10B
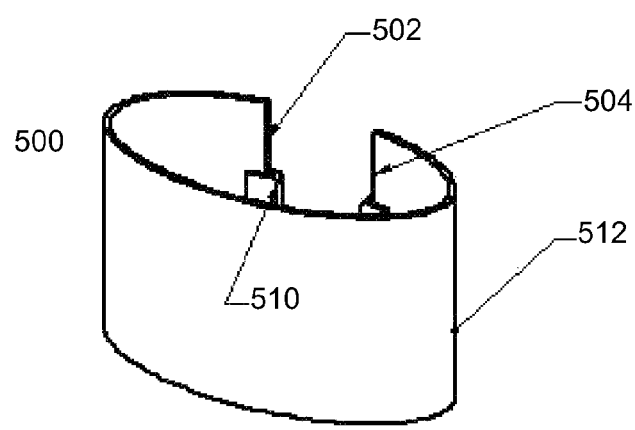
FIG. 11

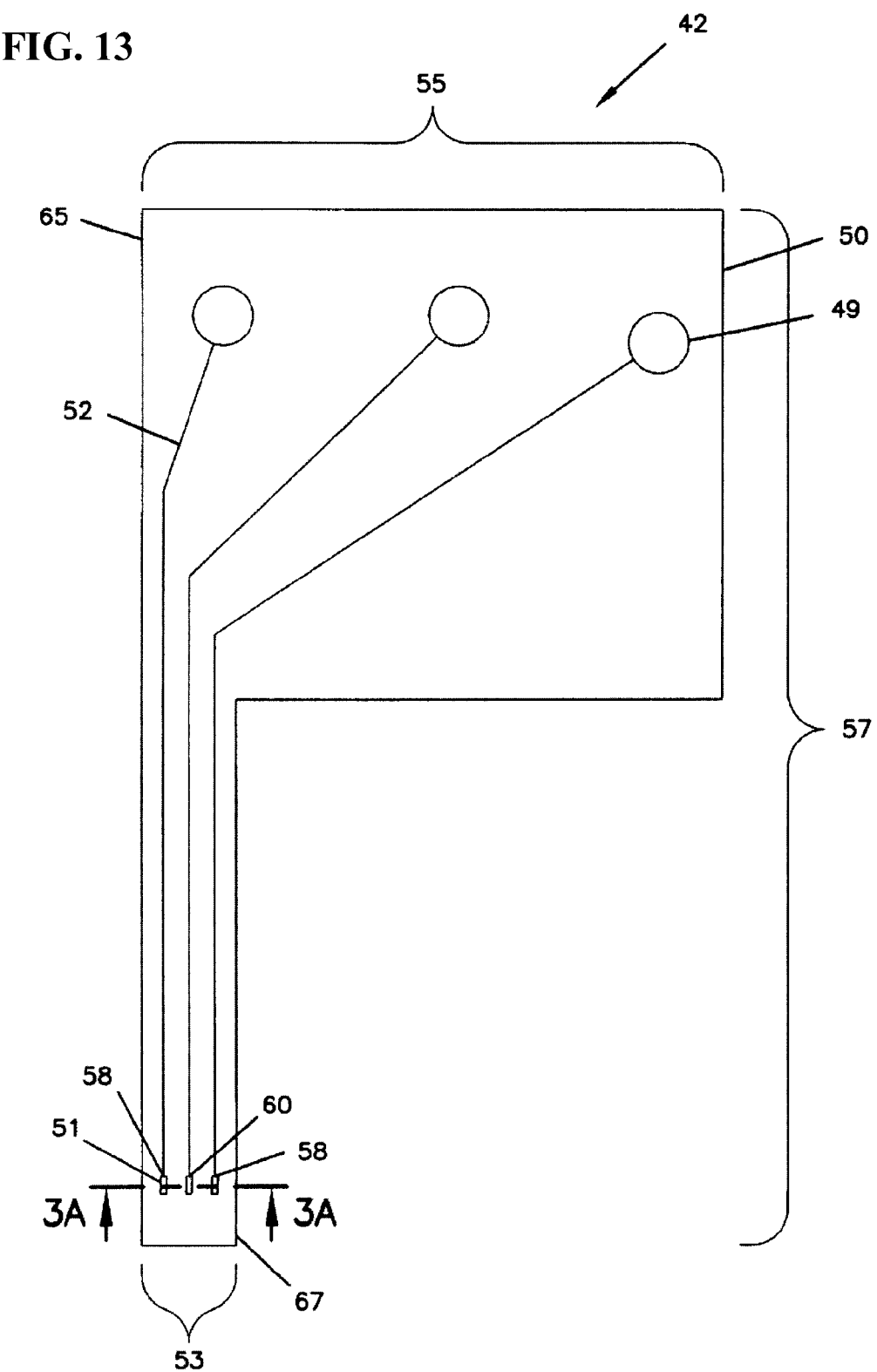

ON-BODY MEDICAL DEVICE SECUREMENT

RELATED APPLICATIONS

The present application is a continuation of U.S. patent application Ser. No. 12/610,237 filed Oct. 30, 2009, now U.S. Pat. No. 7,951,080, which is a continuation of U.S. patent application Ser. No. 11/344,434 filed Jan. 30, 2006, now U.S. Pat. No. 7,736,310, entitled "On-Body Medical Device Securement", the disclosures of each of which are incorporated herein by reference for all purposes.

BACKGROUND OF THE INVENTION

There are many instances in which it is necessary to maintain a medical device "on-body", i.e., secured to a body part of a patient, e.g., the arm, abdomen, or elsewhere. One such instance is maintaining a component of an analyte monitoring system, e.g., a continuous analyte monitoring system, on the skin of a patient.

For example, monitoring of the level of glucose or other analytes, such as lactate or oxygen or the like, in certain individuals is vitally important to their health. The monitoring of glucose level is particularly important to individuals with diabetes, as they must determine when insulin is needed to reduce glucose levels in their bodies or when additional sugar is needed to raise the level of glucose in their bodies. In this regard, devices and systems have been developed for continuous or automatic monitoring of analytes, such as glucose, in the blood stream or in interstitial fluid. Many of these analyte measuring devices include a glucose sensor that is configured so that at least a portion of the sensor is positioned below the epidermis, e.g., in a blood vessel or in the subcutaneous tissue of a patient. The sensor communicates information about the glucose level to a component positioned above the skin, where in certain embodiments the component is intended to be maintained on the skin of the patient.

Despite techniques that have been developed to maintain analyte monitoring components and other medical devices on-body, the component may still become dislodged from its fixed position on the skin, e.g., during vigorous exercise, or the by weakening of the adhesive attaching the components on-body over time, and the like. This dislodgement may be a mere inconvenience, or may have severe consequences, e.g., if the dislodgement goes unnoticed for a substantial period of time during which glucose information is prevented from being obtained. Furthermore, the mere possibility of dislodgement is a constant worry to the user.

As interest in maintaining medical devices, e.g., continuous analyte monitoring devices, in a fixed position on a skin surface continues, there is interest in devices and methods for attaching such device to skin.

SUMMARY OF THE INVENTION

Generally, the present invention relates to methods and devices for maintaining a medical device on-body. In certain embodiments, the present invention relates to the continuous and/or automatic in vivo monitoring of the level of an analyte using an analyte sensor and more specifically, devices and methods for maintaining a component of a continuous or automatic analyte sensing system adjacent a body part of a patient, where the analyte sensors include those in which at least a portion of the sensor is positioned partially beneath the epidermal layer of skin. The subject invention is further described with respect to analyte monitoring devices (also referred to herein as "sensors", "analyte sensing devices", and the like) and analyte monitoring systems for exemplary purposes only, where such description is in no way intended to limit the scope of the invention. It is understood that the subject invention is applicable to any medical device in which at least a portion of the device is intended to be maintained in place on a patient.

Embodiments include devices and methods for maintaining medical devices, e.g., on-body analyte sensor control units, in place and include one or more on-body securement elements. In certain embodiments, first and second on-body securement elements are employed, where the two elements are used together to maintain a medical device such as an on-body sensor control unit in place on a patient. First and second on-body securement elements may be used in a layered construction such that at least a portion of a medical device of interest is sandwiched between the two securement elements to hold the medical device on a body part.

One or both elements may include adhesive for attachment to skin and/or to the other element and/or the medical device (e.g., an on-skin sensor control unit). In certain embodiments, an on-body securement element includes an adhesive area and a non adhesive area. The non adhesive area may be an opening in the securement element, a pocket or other surface or the like that does not have adhesive. The area that does not include adhesive may approximate the size and shape of at least a portion of the medical device to be maintained in place with the securement element so that the non adhesive area may encompass the medical device. In embodiments that include an opening, the opening is positionable around the medical device so as not to completely cover it.

Embodiments include on-body securement elements that are easy to use, e.g., that are easy to position on a body part even in instances in which the area of the body part on which it is desired to position the medical device is not within the direct line of site of the individual performing the positioning. In certain embodiments, a securement element may include one or more release liners adapted to facilitate ease of use, where in some embodiments a plurality of release liners are included and arranged for easy removal from, and positioning of, the securement element.

Also provided are systems and kits.

BRIEF DESCRIPTION OF THE DRAWINGS

The invention may be more completely understood in consideration of the following detailed description of various embodiments of the invention in connection with the accompanying drawings, in which:

FIG. 7A is a top view of one embodiment of an on-skin sensor control unit, according to one embodiment of the invention;

FIG. 8A is a top view of another embodiment of an on-skin sensor control unit and a sensor, according to one embodiment of the invention;

FIG. 9A is an exemplary embodiment of an on-body securement patch according to one embodiment of invention;

FIG. 9B is an exemplary embodiment of an on-body securement patch that includes a medical device placement area according to one embodiment of the invention;

FIG. 10A is an exemplary embodiment of an on-body securement band according to one embodiment of the subject invention;

FIG. 10B is an exemplary embodiment of an on-body securement band that includes a medical device placement area, according to one embodiment of the subject invention;

FIG. 11 is an exemplary embodiment of an on-body securement band or cuff, according to one embodiment of the subject invention;

FIG. 13 is a top view of one embodiment of an analyte sensor, according to one embodiment of the invention;

DETAILED DESCRIPTION OF THE INVENTION

Figure 1:
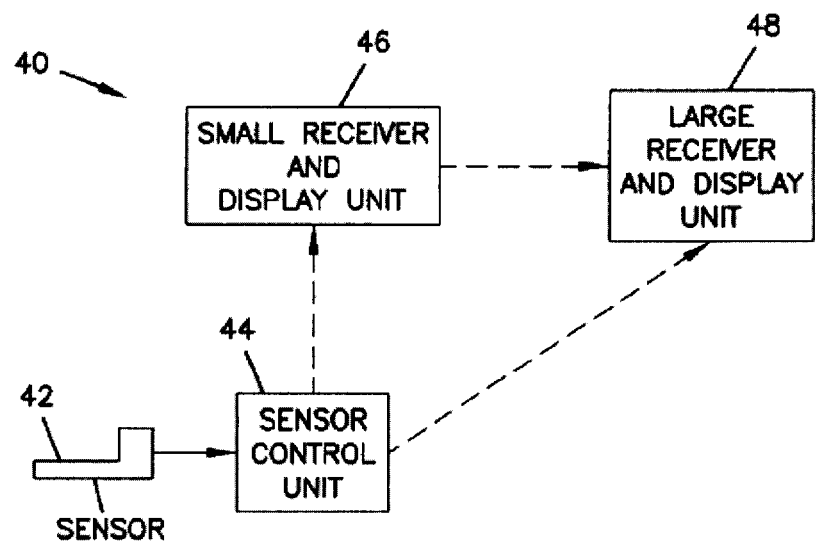
FIG. 1 shows a block diagram of an exemplary embodiment of an analyte monitor using an implantable analyte sensor, according to one embodiment of the invention.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges as also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise.

"May" refers to optionally, and when two or more items (for example, elements or processes) are referenced by an alternative "or", this indicates that either could be present separately or any combination of them could be present together except where the presence of one necessarily excludes the other or others.

Any recited method can be carried out in the order of events recited or in any other order which is logically possible. Reference to a singular item, includes the possibility that there are plural of the same item present.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

As summarized above, the present invention is related to devices and methods for maintaining a medical device in place on the body of a patient. The invention is primarily described herein with respect to maintaining an analyte sensing device and more particularly an on-body analyte control unit adapted for use with an analyte sensor in place on a patient for exemplary purposes only, where such description is in no way intended to limit the scope of the invention. It is to be understood that the invention may be used with a variety of medical devices intended to be maintained in place on a patient. For example, the subject invention may be used to secure an infusion set, e.g., of an insulin pump or the like, in place on the body of a patient.

The present invention is applicable to any analyte monitoring system such as those using a sensor wherein at least a portion of the sensor is positionable beneath the skin of the user for the in vivo determination of a concentration of an analyte, such as glucose, lactate, and the like, in a body fluid. Additional analytes that may be determined include but are not limited to, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

A sensor may be, for example, subcutaneously positionable in a patient for the continuous or periodic monitoring of an analyte in a patient's interstitial fluid. This may be used to infer the glucose level in the patient's bloodstream. The sensors also include in vivo analyte sensors insertable into a vein, artery, or other portion of the body containing fluid. These sensors may be configured for monitoring the level of the analyte over a time period which may range from minutes, hours, days, weeks, or longer. Of interest are analyte sensors, such as glucose sensors, that are capable of providing analyte data for about one hour or more, e.g., about a few hours or more, e.g., about a few days of more, e.g., about three or more days, e.g., about five days or more, e.g., about seven days or more, e.g., about several weeks or months.

Analyte monitoring systems generally include, at a minimum, an analyte sensor and a control unit, where in many embodiments the control unit is intended to be held in place on a body part of the patient. In certain embodiments, a system may only include a sensor and control unit. These analyte monitoring systems may be utilized under a variety of conditions. The particular configuration of a sensor and other units used in an analyte monitoring system may depend on the use for which the sensor and system are intended and the conditions under which the sensor and system will operate. As noted above, embodiments include a sensor configured for positioning into the body of a patient or user. The term "positioning" is meant broadly to include wholly implantable sensors and sensors in which only a portion of which is positioned under the skin and a portion of which resides above the skin, e.g., for contact to a transmitter, receiver, transceiver, processor, etc.

For example, positioning of a sensor may be made in the arterial or venous systems for direct testing of analyte levels in blood. Alternatively, a sensor may be positioned in the interstitial tissue for determining the analyte level in interstitial fluid. This level may be correlated and/or converted to analyte levels in blood or other fluids. Sensors may also be positioned in other regions of the body to determine analyte levels in other fluids. Examples of suitable sensors for use in the analyte monitoring systems of the invention are described herein and in, for example, U.S. Pat. Nos. 6,134,461, 6,175, 752, and elsewhere.

Figure 2:
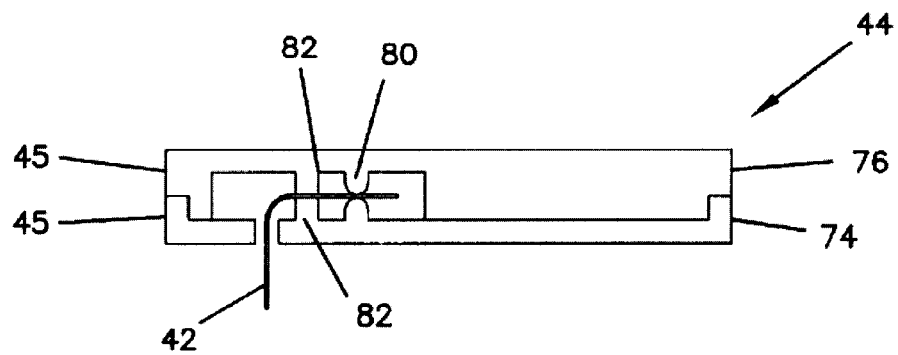
FIG. 2 is a cross-sectional view of an embodiment of an on-skin sensor control unit, according to one embodiment of the invention.
Figure 3:
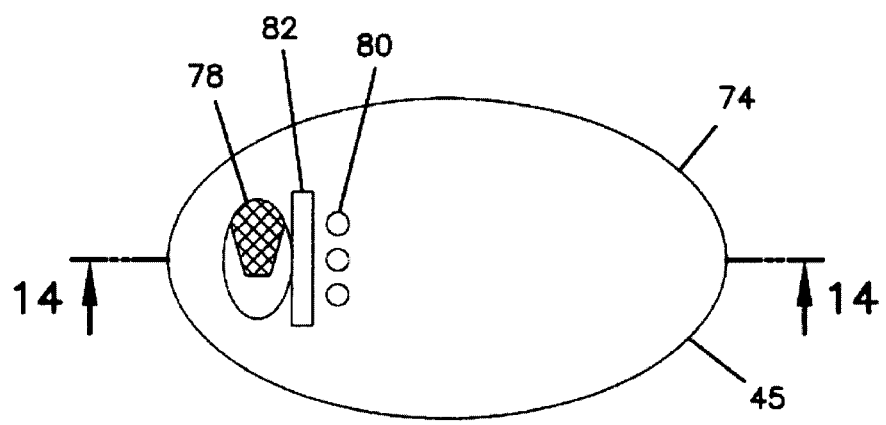
FIG. 3 is a top view of a base of the on-skin sensor control unit of FIG. 2.
Figure 4:
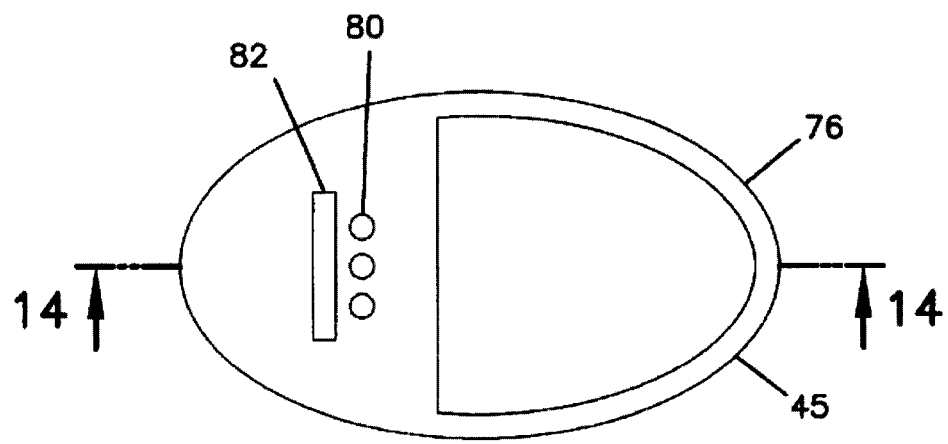
FIG. 4 is a bottom view of a cover of the on-skin sensor control unit of FIG. 2.

FIG. 1 illustrates in block diagram form, an exemplary embodiment of an analyte monitoring system 40. Analyte monitoring system 40 includes, at minimum, a sensor 42, at least a portion of the sensor which is configured for positioning (e.g., subcutaneous, venous, or arterial positioning) into a patient, and a sensor control unit 44. Sensor 42 is coupleable to sensor control unit 44 which, as noted above, is intended to be worn by the patient. Sensor control unit 44 operates sensor 42, including, for example, providing a voltage across the electrodes of the sensor and collecting signals from the sensor. In certain embodiments, the control unit is shaped and sized to be concealable. For example, in certain embodiments, on-skin sensor control unit 44 has a thin, oval shape to enhance concealment, as illustrated in FIGS. 3 and 4. However, other shapes and sizes may be used. On-skin sensor control unit 44 includes a housing 45, as illustrated in FIGS. 2-4 for example.

Sensor control unit 44 may evaluate the signals from sensor 42 and/or transmit the signals to one or more optional receiver/display units 46, 48 for evaluation. Sensor control unit 44 and/or receiver/display units 46, 48 may display or otherwise communicate the current level of the analyte. Furthermore, sensor control unit 44 and/or receiver/display units 46, 48 may indicate to the patient, via, for example, an audible, visual, or other sensory-stimulating alarm, when the level of the analyte is at or near a threshold level. In some embodiments, an electrical shock may be delivered to the patient as a warning through one of the electrodes or the optional temperature probe of the sensor. For example, if glucose is monitored then an alarm may be used to alert the patient to a hypoglycemic or hyperglycemic glucose level and/or to impending hypoglycemia or hyperglycemia.

Sensor 42 and the electronic components within on-skin sensor control unit 44 are coupled via conductive contacts 80. The one or more working electrodes 58, counter electrode 60 (or counter/reference electrode), optional reference electrode 62, and optional temperature probe 66 (see for example FIGS. 13-17) are attached to individual conductive contacts 80. In some embodiments, the conductive contacts are provided on the exterior of the housing (see for example FIGS. 7A and 7B) and in other embodiments the conductive contacts are provided on the interior of the housing, e.g., within a hollow or recessed region. In the illustrated embodiment of FIGS. 2-4, the conductive contacts 80 are provided on the interior of the on-skin sensor control unit 44.

Figure 5A:
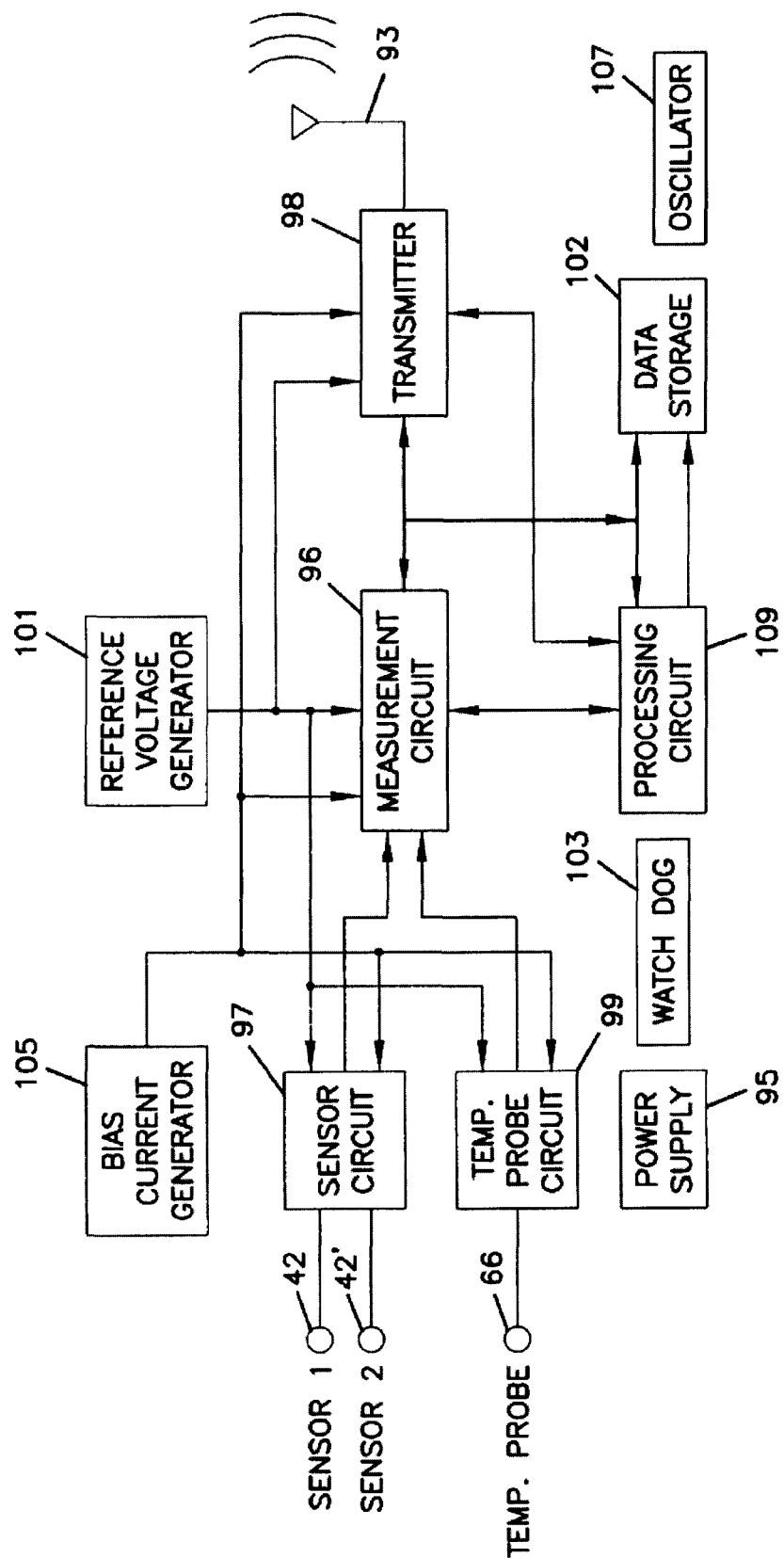
FIG. 5A is a block diagram of an embodiment of an on-skin sensor control unit, according to one embodiment of the invention.

The on-skin sensor control unit may include at least a portion of the electronic components that operate the sensor and the analyte monitoring device system. One embodiment of the electronics in the on-skin control unit 44 is illustrated as a block diagram in FIG. 5A. The electronic components of on-skin sensor control unit 44 may include a power supply 95 for operating the on-skin control unit and the sensor, a sensor circuit 97 for obtaining signals from and operating the sensor, a measurement circuit 96 that converts sensor signals to a desired format, and a processing circuit 109 that, at minimum, obtains signals from the sensor circuit 97 and/or measurement circuit 96 and provides the signals to an optional transmitter 98. In some embodiments, processing circuit 109 may also partially or completely evaluate the signals from the sensor and convey the resulting data to the optional transmitter 98 and/or activate an optional alarm system 94 (see FIG. 5B) if the analyte level exceeds a threshold. Processing circuit 109 often includes digital logic circuitry.

On-skin sensor control unit 44 may optionally contain a transmitter or transceiver 98 for transmitting the sensor signals or processed data from processing circuit 109 to a receiver (or transceiver)/display unit 46, 48; a data storage unit 102 for temporarily or permanently storing data from processing circuit 109; a temperature probe circuit 99 for receiving signals from and operating a temperature probe 66; a reference voltage generator 101 for providing a reference voltage for comparison with sensor-generated signals; and/or a watchdog circuit 103 that monitors the operation of the electronic components in the on-skin sensor control unit. Moreover, sensor control unit 44 may include a bias current generator 105 to correctly bias analog and digital semiconductor devices, an oscillator 107 to provide a clock signal, and a digital logic and timing component to provide timing signals and logic operations for the digital components of the circuit.

Figure 5B:
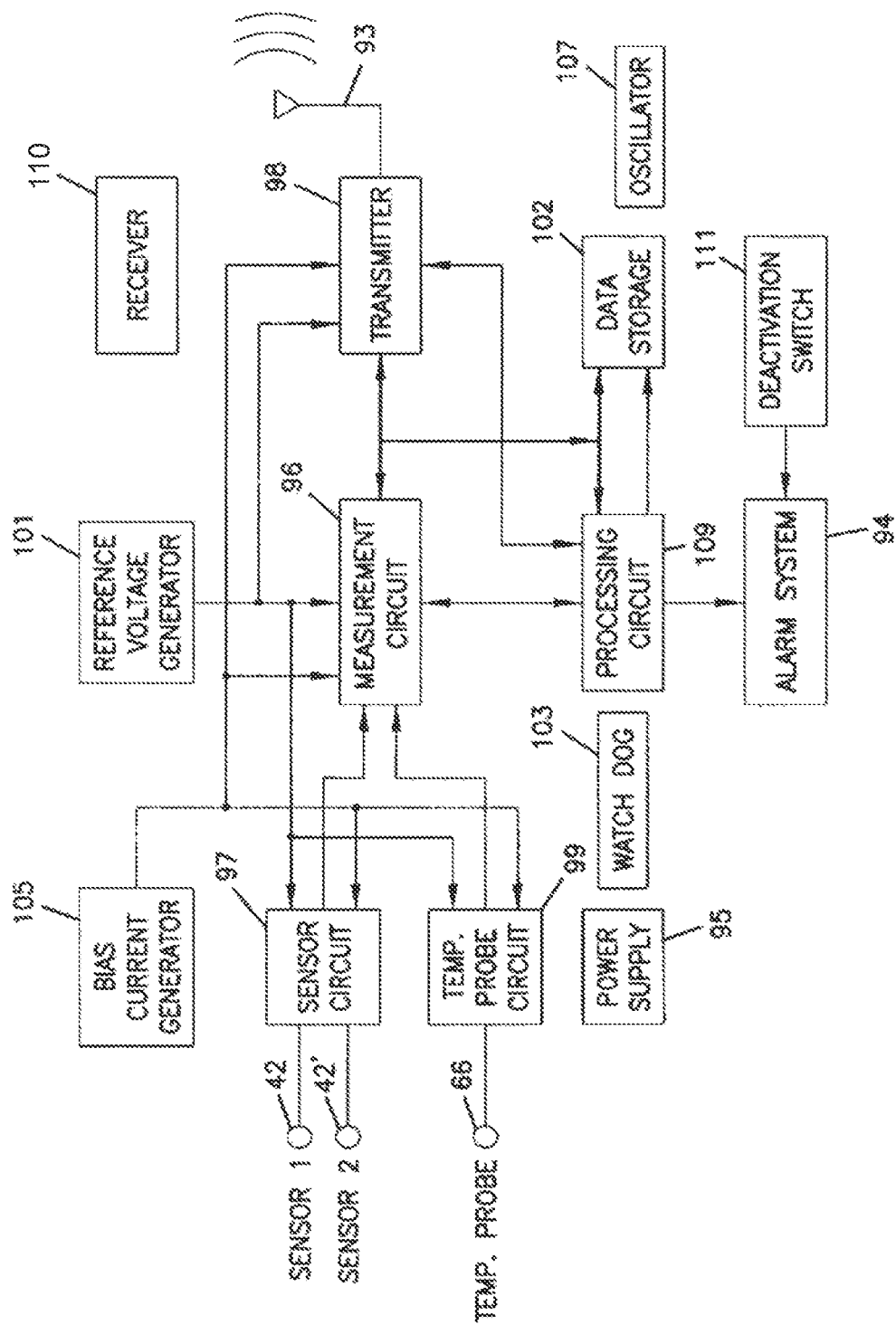
FIG. 5B is a block diagram of an embodiment of an on-skin sensor control unit, according to one embodiment of the invention.

FIG. 5B illustrates a block diagram of another exemplary on-skin sensor control unit 44 that also includes optional components such as a receiver (or transceiver) 110 to receive, for example, calibration data; a calibration storage unit (not shown) to hold, for example, factory-set calibration data, calibration data obtained via the receiver 110 and/or operational signals received, for example, from a receiver/display unit 46, 48 or other external device; an alarm system 94 for warning the patient; and a deactivation switch 111 to turn off the alarm system.

The electronics in the on-skin sensor control unit 44 and the sensor 42 may be operated using a power supply 95. Sensor control unit 44 may also optionally include a temperature probe circuit 99. The output from sensor circuit 97 and optional temperature probe circuit is coupled into a measurement circuit 96 that obtains signals from sensor circuit 97 and optional temperature probe circuit 99 and, at least in some embodiments, provides output data in a form that, for example can be read by digital circuits.

In some embodiments, the data from processing circuit 109 is analyzed and directed to an alarm system 94 (see FIG. 5B) to warn the user. For example, an alarm may notify a patient of a hypo- or hyperglycemic event.

In some embodiments, the data (e.g., a current signal, a converted voltage or frequency signal, or fully or partially analyzed data) from processing circuit 109 is transmitted to one or more receiver/display units 46, 48 using a transmitter 98 in on-skin sensor control unit 44. The transmitter has an antenna 93, such as a wire or similar conductor, formed in housing 45.

In addition to a transmitter 98, an optional receiver 110 may be included in the on-skin sensor control unit 44. In some cases, transmitter 98 is a transceiver, operating as both a transmitter and a receiver. Receiver 110 (and/or receiver display/units 46, 48) may be used to receive calibration data for the sensor 42. The calibration data may be used by processing circuit 109 to correct signals from sensor 42. This calibration data may be transmitted by receiver/display unit 46, 48 or from some other source such as a control unit in a doctor's office. The on-skin sensor control unit 44 may include an optional data storage unit 102 which may be used to hold data (e.g., measurements from the sensor or processed data).

In certain embodiments, on-skin sensor control unit 44 includes a sensor port through which a sensor enters the subcutaneous tissue of the patient. A sensor may be inserted into the subcutaneous tissue of the patient through the sensor port. The on-skin sensor control unit may then be placed on the skin of the patient with a sensor being threaded through the sensor port. If the housing of the sensor has, for example, a base and a cover, then the cover may be removed to allow the patient to guide the sensor into the proper position for contact with conductive contacts 80. Alternatively, if the conductive contacts are within the housing the patient may slide the sensor into the housing until contact is made between the contact pads of the sensor and the conductive contacts. The sensor control unit may have a structure which obstructs the sliding of the sensor further into the housing once the sensor is properly positioned with the contact pads in contact with the conductive contacts. In other embodiments, the conductive contacts are on the exterior of the housing. In these embodiments, the patient guides the contacts pads of the sensor into contact with the conductive contacts of the control unit. In some cases, a guiding structure may be provided on the housing which guides the sensor into the proper position. An example of such a structure includes a set of guiding rails extending from the housing and having the shape of the sensor.

One or more receiver/display units 46, 48 may be provided with the analyte monitoring device 40 for easy access to the data generated by the sensor 42 and may, in some embodiments, process the signals from the on-skin sensor control unit 44 to determine the concentration or level of analyte in the subcutaneous tissue. The receiver may be a transceiver. Receivers may be palm-sized and/or may be adapted to fit on a belt or within a bag or purse that the patient carries.

Figure 20:
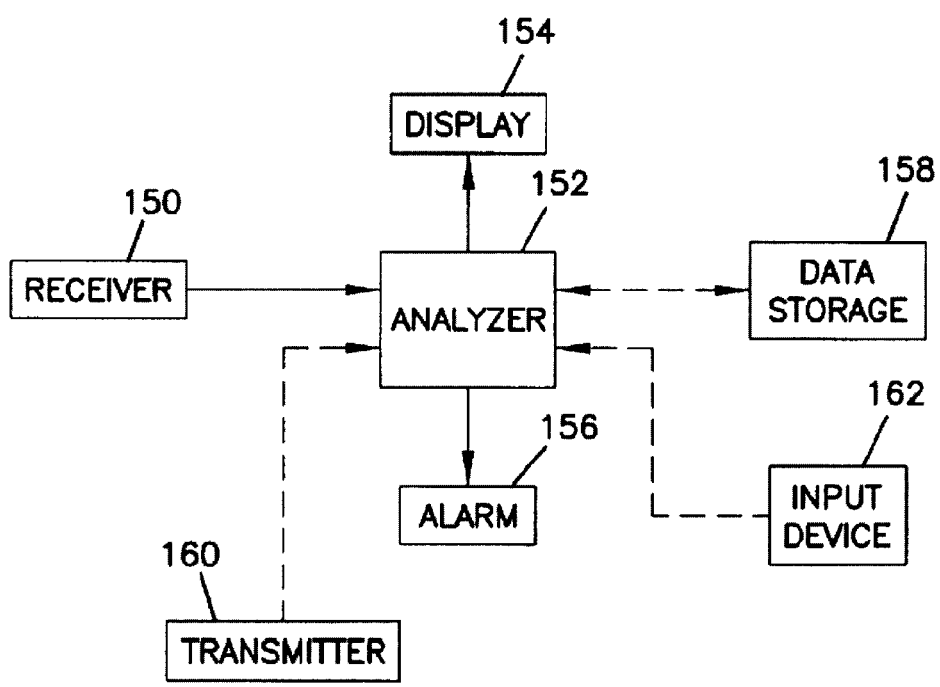
FIG. 20 is a block diagram of one embodiment of a receiver/display unit, according to one embodiment of the invention.

The receiver/display units 46, 48, as illustrated in block form at FIG. 20, typically include a receiver 150 to receive data from the on-skin sensor control unit 44, an analyzer 152 to evaluate the data, a display 154 to provide information to the patient, and an alarm system 156 to warn the patient when a condition arises. The receiver/display units 46, 48 may also optionally include a data storage device 158, a transmitter 160, and/or an input device 162. Data received by the receiver 150 may then be sent to an analyzer 152.

The output from the analyzer 152 may be provided to a display 154. The receiver/display units 46, 48 may also include a number of optional items such as a data storage unit 158 to store data, a transmitter 160 which can be used to transmit data, and an input device 162, such as a keypad or keyboard.

In certain embodiments, the receiver/display unit 46, 48 is integrated with a calibration unit (not shown). For example, the receiver/display unit 46, 48 may, for example, include a conventional blood glucose monitor. Devices may be used including those that operate using, for example, electrochemical and colorimetric blood glucose assays, assays of interstitial or dermal fluid, and/or non-invasive optical assays. When a calibration of the implanted sensor is needed, the patient uses the integrated in vitro monitor to generate a reading. The reading may then, for example, automatically be sent by the transmitter 160 of the receiver/display unit 46, 48 to calibrate the sensor 42.

In certain embodiments, analyte data (processed or not) may be communicated, e.g., forwarded (such as by communication) to a remote location such as a doctor's office if desired, and received there for further use (such as further processing).

Figure 6:
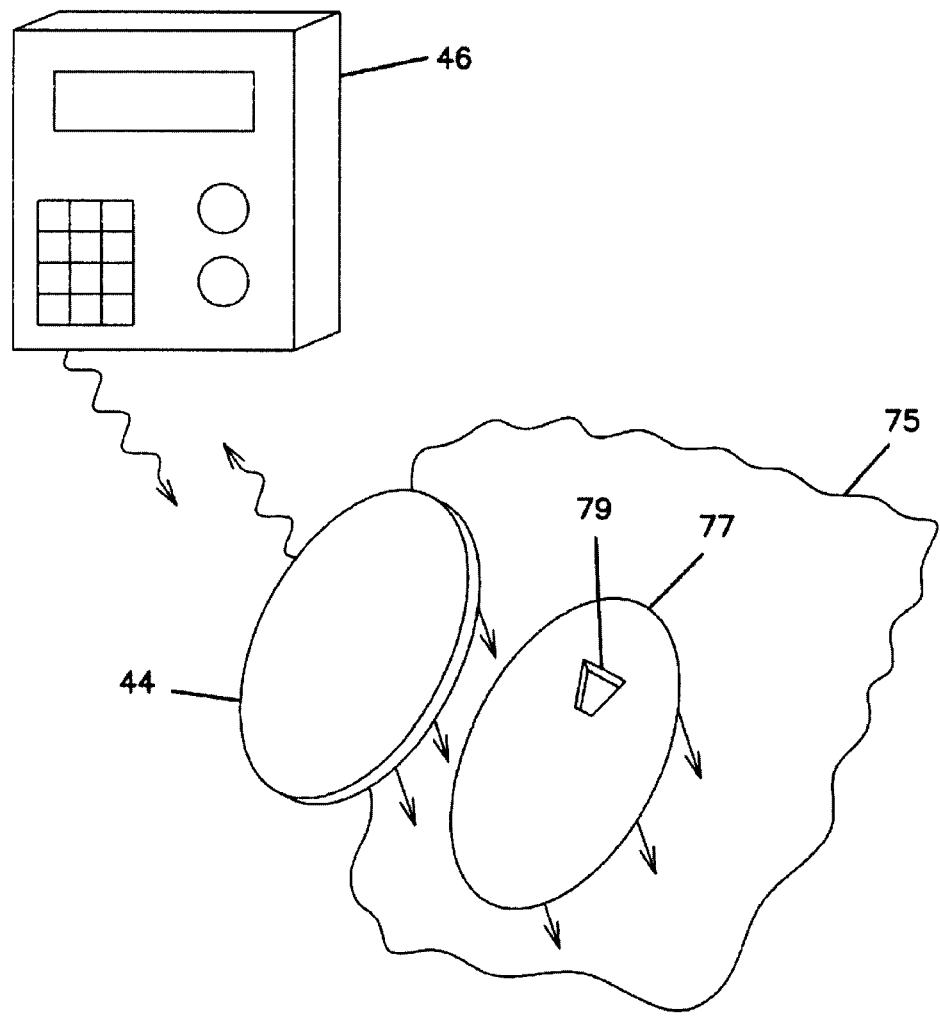
FIG. 6 is a perspective view of the on-skin sensor control unit of FIG. 2 on the skin of a patient.

As described, on-skin sensor control unit 44 is intended to be worn "on-body" by the patient, e.g., attached directly or indirectly to the skin 75 of the patient, as illustrated for example in FIG. 6. The subject invention provides methods and devices for such on-body placement and securement. As described in greater detail below, certain embodiments include only one on-body securement element and certain embodiments include at least a first on-body securement element and a second on-body securement element. A first securement element may be adapted for attachment to a skin surface, e.g., may be an adhesive-containing element or the like, and also to on-skin control unit. For example, a first side may include adhesive for attachment to skin and a second side may be adapted for mating with a control unit. A second securement element may be adapted to be positionable over at least a portion of the first element, including a first element/control unit structure. In some embodiments, only one on-body securement elements may be used or one may be used in certain instances and the other or both may be used in certain other instances. For example, a first element may be used for everyday use, and the second element may be included and used with the first (or used alone) in certain instances, e.g., vigorous activities such as exercising and the like.

Referring again to FIG. 6, on-skin sensor control unit 44 may be attached by adhering the on-skin sensor control unit 44 directly to the skin 75 of the patient with an adhesive provided on at least a portion of the housing 45 of the on-skin sensor control unit 44 which contacts the skin 75 or by suturing the on-skin sensor control unit 44 to the skin 75 through suture openings (not shown) in the sensor control unit 44.

In other embodiments, a mounting unit 77 is employed to attach the housing 45 of the on-skin sensor control unit 44 to the skin 75. Mounting unit 77 may be part of the on-skin sensor control unit 44 or may be separate. One example of a suitable mounting unit is a double-sided adhesive strip, one side of which is adhered to a surface of the skin of the patient and the other side is adhered to the on-skin sensor control unit 44. In this embodiment, the mounting unit 77 may have an optional opening 79 which is large enough to allow insertion of sensor 42 through opening 79 for electrical contact with the control unit. Alternatively, the sensor may be inserted through a thin adhesive and into the skin.

A variety of adhesives may be used to adhere the on-skin sensor control unit 44 to the skin 75 of the patient, either directly or using the mounting unit 77, including, for example, pressure sensitive adhesives (PSA) or contact adhesives. An adhesive is usually chosen which is not irritating to all or a majority of patients for at least the period of time that a particular sensor 42 is implanted in the patient, e.g., may be hypoallergenic adhesive. Alternatively, a second adhesive or other skin-protecting compound may be included with the mounting unit so that a patient, whose skin is irritated by the adhesive on the mounting unit 77, may cover his skin with the second adhesive or other skin-protecting compound and then place the mounting unit 77 over the second adhesive or other skin-protecting compound. This should substantially prevent the irritation of the skin of the patient because the adhesive on the mounting unit 77 is no longer in contact with the skin, but is instead in contact with the second adhesive or other skin-protecting compound. Adhesives that may be used includes, but is not limited to acrylic adhesives, and the like, e.g., a polyurethane membrane coated with a layer of an acrylic adhesive such as TEGADERM from 3M Corporation.

Figure 7B:
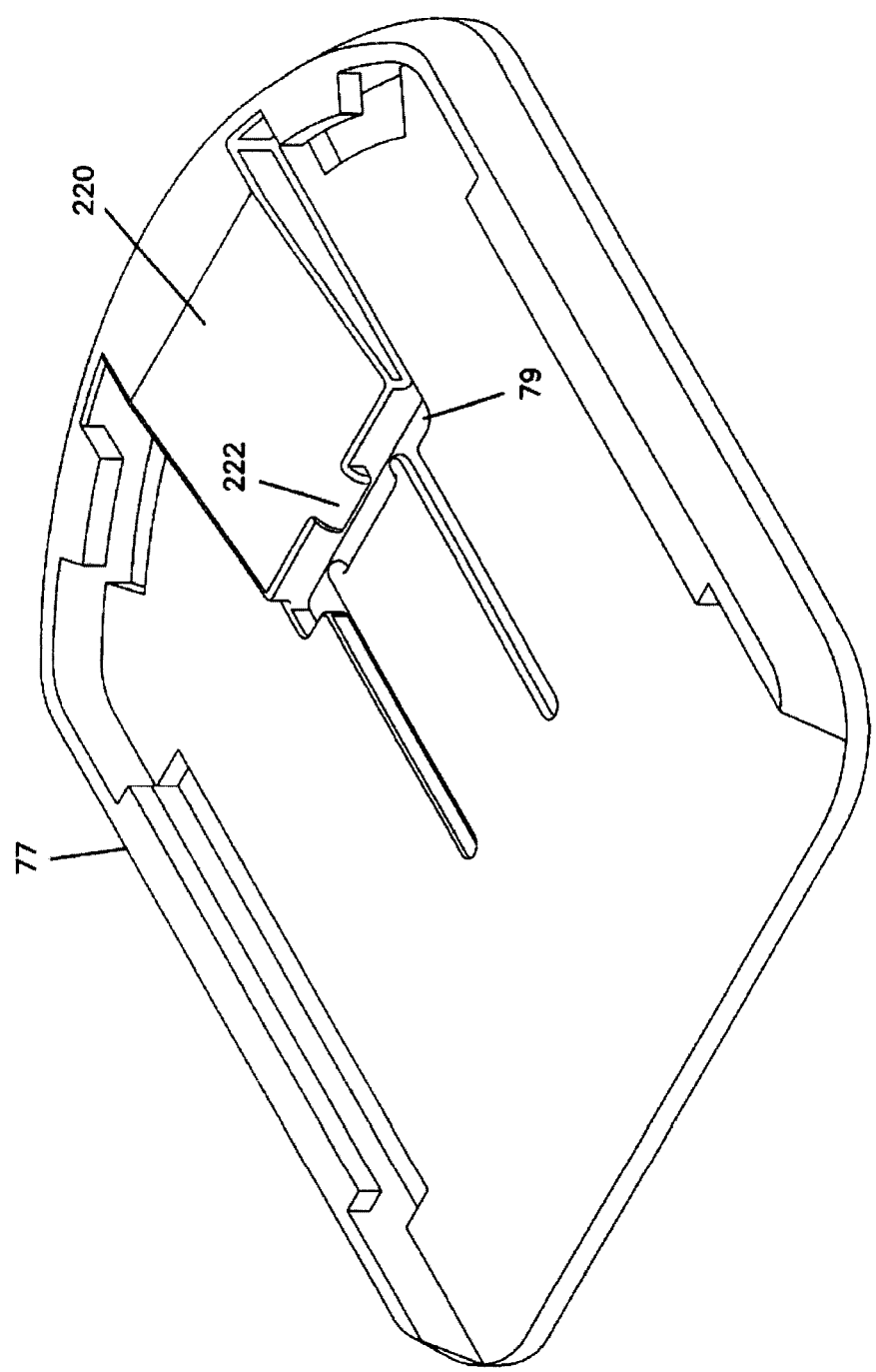
FIG. 7B is a top view of one embodiment of a mounting unit of the on-skin sensor control unit of FIG. 7A.

Another embodiment of a mounting unit 77 that may be used in an on-skin sensor control unit 44 is illustrated in FIGS. 7A and 7B. Mounting unit 77 and housing 45 of on-skin sensor control unit 44 are mounted together in, for example, an interlocking manner, as shown in FIG. 7A. Mounting unit 77 is formed, for example, using plastic or polymer materials, including, for example, polycarbonate, polyvinyl chloride, polyethylene, polypropylene, polystyrene, ABS polymers, and copolymers thereof. The mounting unit 77 may be formed using a variety of techniques including, for example, injection molding, compression molding, casting, and other molding methods.

The mounting unit 77 may include an adhesive on a bottom surface to adhere to the skin of the patient or mounting unit 77 used in conjunction with, for example, double-sided adhesive tape or the like. The mounting unit 77 may include an opening 79 through which the sensor 42 is inserted, as shown for example in FIG. 7B. Mounting unit 77 may also include a support structure 220 for holding a sensor in place and against the conductive contacts 80 of the on-skin sensor control unit. Mounting unit 77, also, optionally, includes a positioning structure 222, such as an extension of material from the mounting unit, that corresponds to a structure (not shown), such as an opening, on a sensor 42 to facilitate proper positioning of the sensor, for example, by aligning the two complementary structures.

Figure 8B:
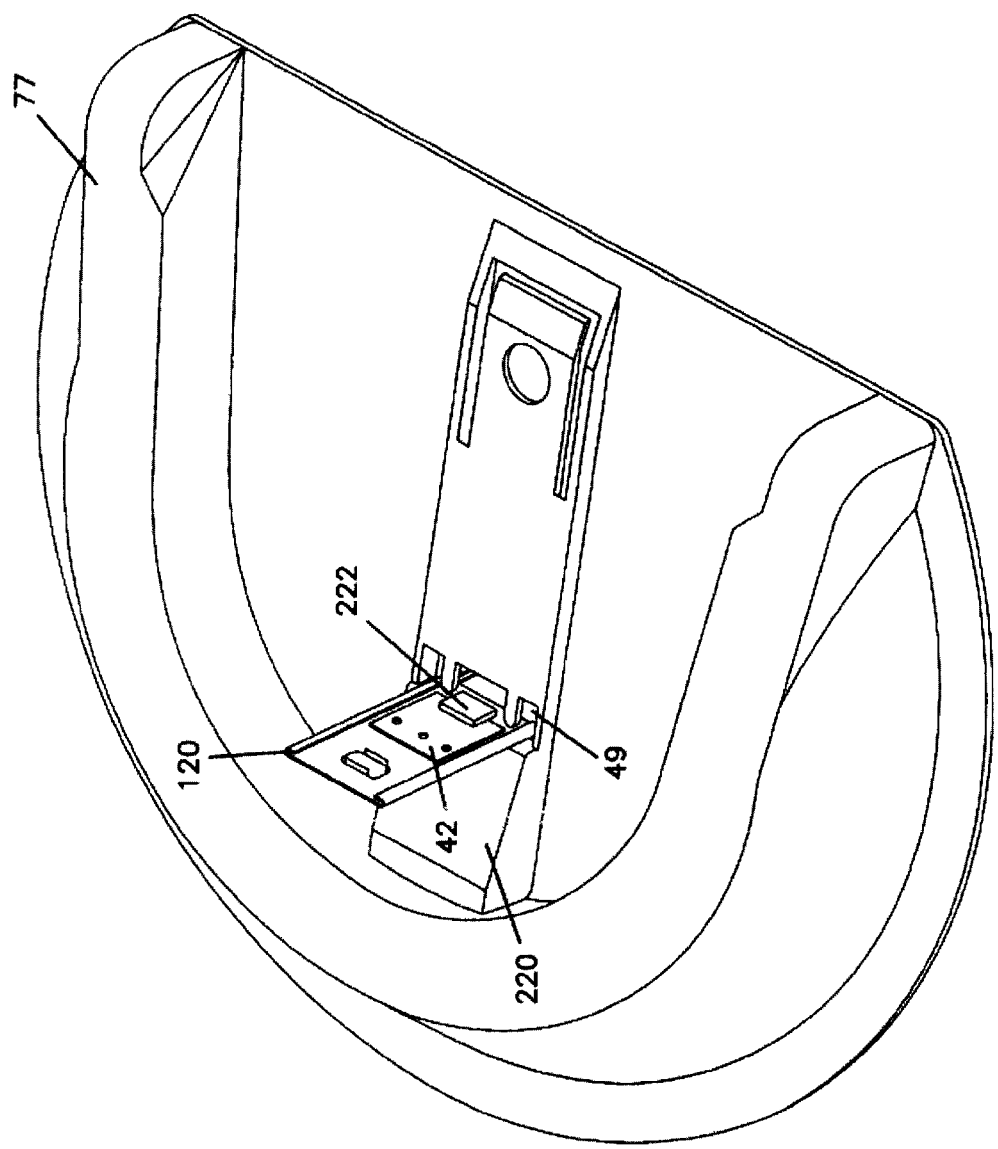
FIG. 8B is a top view of one embodiment of a mounting unit of the on-skin sensor control unit of FIG. 8A.
Figure 8C:
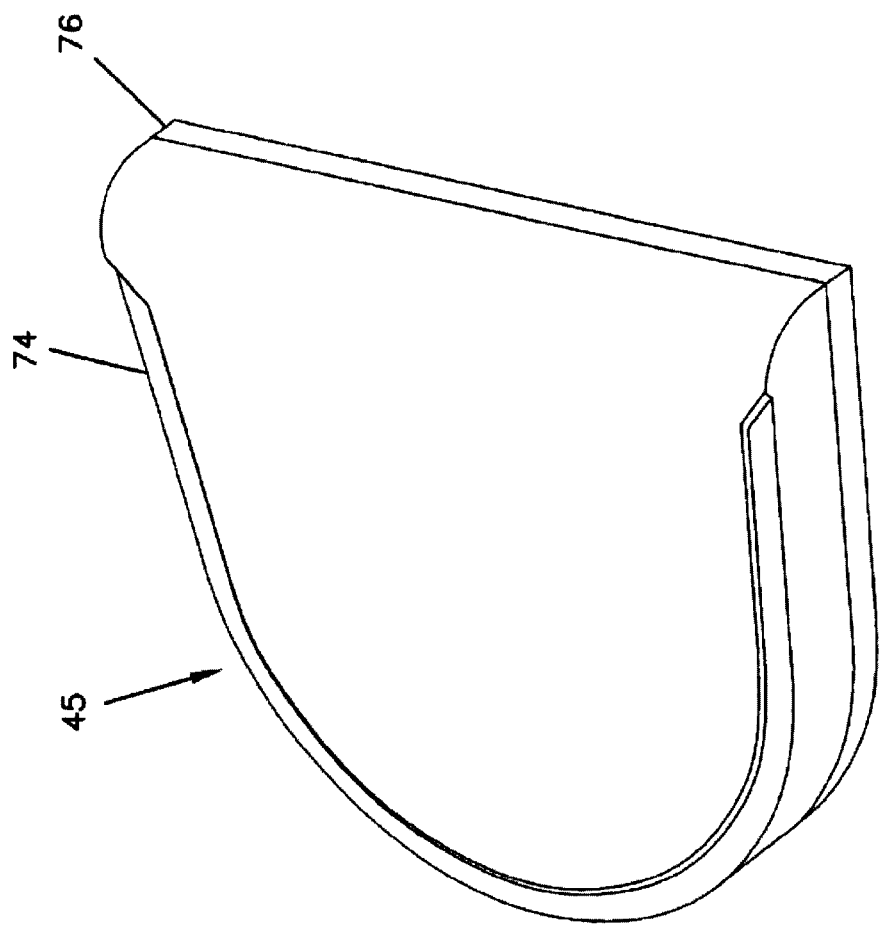
FIG. 8C is a top view of one embodiment of a housing for at least a portion of the electronics of the on-skin sensor control unit of FIG. 8A.
Figure 8D:
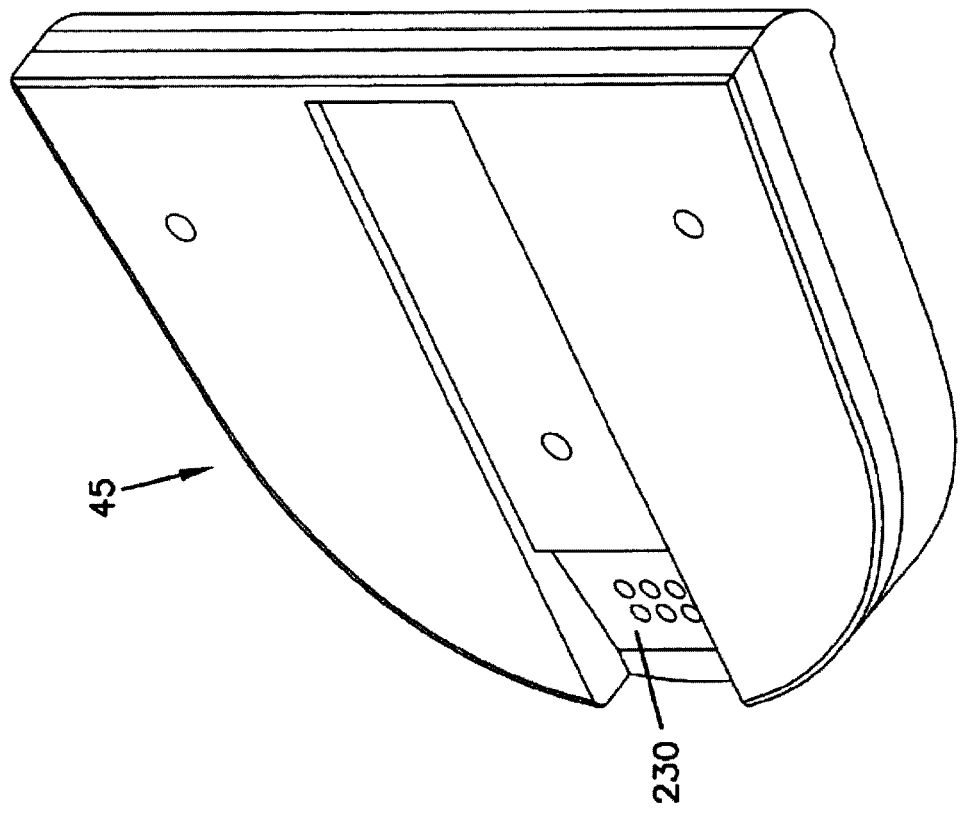
FIG. 8D is a bottom view of the housing of FIG. 8C.

In another embodiment, a coupled mounting unit 77 and housing 45 of an on-skin sensor control unit 44 is provided on an adhesive patch 204 with an optional cover 206 to protect and/or confine housing 45 of the on-skin sensor control unit 44, as illustrated in FIG. 8A. The optional cover may contain an adhesive or other mechanism for attachment to the housing 45 and/or mounting unit 77. Mounting unit 77 typically includes an opening 49 through which a sensor 42 is disposed, as shown in FIG. 8B. Opening 49 may optionally be configured to allow insertion of the sensor 42 through the opening using an insertion device or insertion gun. Housing 45 of on-skin sensor control unit 44 has a base 74 and a cover 76, as illustrated in FIG. 8C. A bottom view of housing 45, as shown in FIG. 8D, illustrates ports 230 through which conductive contacts (not shown) extend to connect with contact pads on the sensor 42. A board (not shown) for attachment of circuit components may optionally be provided within on-skin sensor control unit 44.

In some embodiments, the adhesive on an on-skin sensor control unit 44 and/or on any of the embodiments of mounting unit 77 is water resistant or waterproof to permit activities such as showering and/or bathing while maintaining adherence of the on-skin sensor control unit to the skin of the patient and, at least in some embodiments, preventing water from penetrating into the sensor control unit. The use of a water resistant or waterproof adhesive combined with a water resistant or waterproof housing 45 protects the components in sensor control unit 44 and the contact between conductive contacts 80 and sensor 42 from damage or corrosion. An example of a non-irritating adhesive that repels water is TEGADERM.

As described above, in certain embodiments an on-body securement element may be adapted to be positionable about at least a portion of the control unit and may be used in addition to, or instead of, any securement element described herein. For example, a first on-body securement element may be used that is attachable to a body part, e.g., includes an adhesive for attachment to the skin. The adhesive may be directly on the control unit or may be a separate component, e.g., a mounting unit or an adhesive patch to which a mounting unit/control unit is attachable, etc. The on-body securement element, if it includes adhesive, may be adapted to adhesively attach to the skin and/or mount and/or control unit, and/or a first adhesive patch positioned adjacent the skin and upon which the mount and/or control unit resides, e.g., in certain embodiments with a control unit held therebetween.

A second securement element may be included and may be a securement patch or band and may or may not include adhesive. FIGS. 9-11 show exemplary embodiments of on-body securement elements. Securement elements 300 and 310 of FIGS. 9A and 9B, respectively, are in the form of securement patches, e.g., adhesive patches. The adhesive patches may include adhesive on a backing layer. Securement elements 400 and 410 of FIGS. 10A and 10B, respectively, are in the form of securement bands and embodiment 500 of FIG. 11 is in the form of a securement strap or cuff. Elements 300 and 400 of FIGS. 9A and 10A, respectively, are substantially the same as elements 310 and 410 of FIGS. 9B and 10B, respectively, except the embodiments of FIGS. 9A and 10A do not include a control unit area 315 and 415, respectively (it is understood that embodiment 500 of FIG. 11 may also include a control unit area (not shown)), which may include one or more of: a hole, a covering such as a transparent shield (e.g., non-adhesive), a recess or pouch, or is otherwise a non adhesive area. In those embodiments in which control unit area 315 is an opening in the securement element, the opening provides an area through which a control unit may be positioned so that the control unit is not completely covered by the on-body securement element. In certain embodiments, the securement element may be opaque except for an opening covered with a transparent shield, the shield configured to be positioned over a control unit. The shield may be compressible to allow a user to actuate buttons, knobs, thumbwheels, etc., if provided on the control unit and which may be positioned beneath the shield.

A non adhesive-including area may be particularly relevant if an on-body securement element includes an adhesive-including area. An opening (or otherwise non-adhesive surface)

provides an adhesive-free area which prevents accumulation of adhesive residue on the control unit surface, improving moisture transmission rates and eliminating entrapped pockets that may serve as potential sites for water accumulation. An opening or recess provides a further advantage of providing an easily identifiable reference point for registering the securement element with a control unit so that it may be correctly and easily positioned about the control unit even in instances in which the control unit is not within the direct line of site of the patient. This may be particularly important for patients with diminished hand-eye coordination and/or manual dexterity and/or visual capabilities.

In certain embodiments, an on-body securement element provides mild compression of a body part so that the element does not readily slip off of the patient. The on-body securement element may be further tightened using a fastening strap or other mechanism which cinches the element tighter onto the arm.

In embodiments in which the on-body securement element is a patch, e.g., an adhesive-including patch, as shown for example in FIGS. 9A and 9B, securement patches 300 and 310 include support 312. Certain embodiments may include adhesive. For example, a first on-body securement element in the form of a first adhesive patch attachable to the skin may be employed. The first patch may be adapted for retaining a mounting unit and/or control unit and may be sized to include an extended edge so that once a mount and/or control unit is positioned thereupon, a perimeter edge is available for attachment to a second adhesive patch. Accordingly, a second adhesive patch is positioned either completely over the control unit, e.g., in the case of the embodiments of FIG. 9A, or positioned around the control unit rather than over it (but positioned about the mounting unit or adhesive patch carrying a mounting unit)—using the extended edge of the first adhesive patch as a point of attachment between the first and second patches.

Other securement embodiments may be in the form of an arm band or strap that partially or completely encircle a body part such as an arm, leg, wrist, abdomen, etc., as shown for example in FIGS. 10A, 10B and 11. Analogous to a patch securement element, an arm band or strap securement, if inclusive of adhesive, may be adapted to adhesively attach to the skin and/or mount and/or control unit, and/or a first adhesive patch positioned adjacent the skin and upon which the mount and/or control unit resides.

In certain embodiments, an on-body securement element may be a tubular structure such as securement bands 400 and 410 having supports 412, as shown in FIGS. 10A and 10B, e.g., elasticized tubular elements. In certain embodiments, a securement element may be in the form of a strap or cuff such as securement element 500 having support 512, as shown in FIG. 11. Securement element 500 may include joinable ends 502 and 504 for forming a tubular structure. Opposing ends 502 and 504 may include fasteners 510 to connect the opposing ends together to form a tubular structure and surround a body part of a patient. Fasteners that may be used include but are not limited to snaps, buttons, zippers, hook-and-loop fastener, laces, Velcro®, latches, etc. The fastening system may bring the opposing ends of a securement element in proximity to permit coaptation.

In addition to the support layer and adhesive layer (if present), additional layers may be included. For example, a removable layer may be positioned adjacent to one or more surfaces (e.g., adjacent an adhesive layer surface and/or casting layer surface) of a securement element for protection of the securement element from the environment. For example, a securement element having an adhesive surface may include a peelable release liner adjacent the adhesive surface to maintain the integrity of the adhesive until use and/or a casting layer. In certain embodiments, a securement element may be in the form of a sandwich configuration such as a laminate or the like. A securement element may include adhesive disposed on a backing, the adhesive/backing structure may be sandwiched between two removable layers: a removable release liner adjacent the adhesive and a removable casting layer adjacent the backing. The materials thereof may be any suitable materials, including materials described herein and others. Any suitable materials may be used, where in certain embodiments a release liner is a polyester such as PET or PP, and the like, or siliconized paper (e.g., siliconized Kraft paper), or the like, an adhesive is polyacrylate, silicone, PIB, natural or synthetic rubber or the like, a backing is a polyurethane film, or the like, in the form of films, foams, nonwovens, etc., and the casting layer is PE, or the like.

In certain embodiments, the removable layer(s) may have greater rigidity than the securement element with which it is employed. This relative rigidity may provide structural stability and facilitate peeling-away of the layer from the securement element by the patient. A removable layer such as a release liner may include tabs or the like graspable by a patient.

In certain embodiments, a plurality of release liners is used. A plurality of release liners may increase the ease of removal of the release liners from the securement element and the ease of use of the securement element by providing one-handed, self-application of a securement element.

Figure 12A:
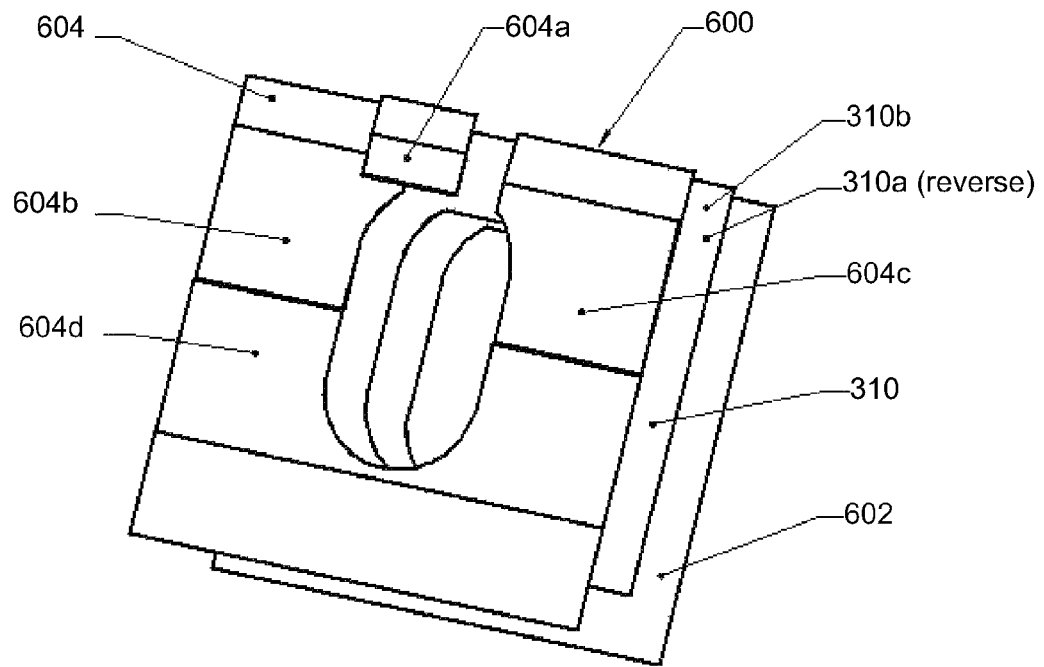
FIG. 12A is an exemplary embodiment of a release liner protective system protecting an adhesive containing a body securement element, according to one embodiment of the subject invention.
Figure 12B:
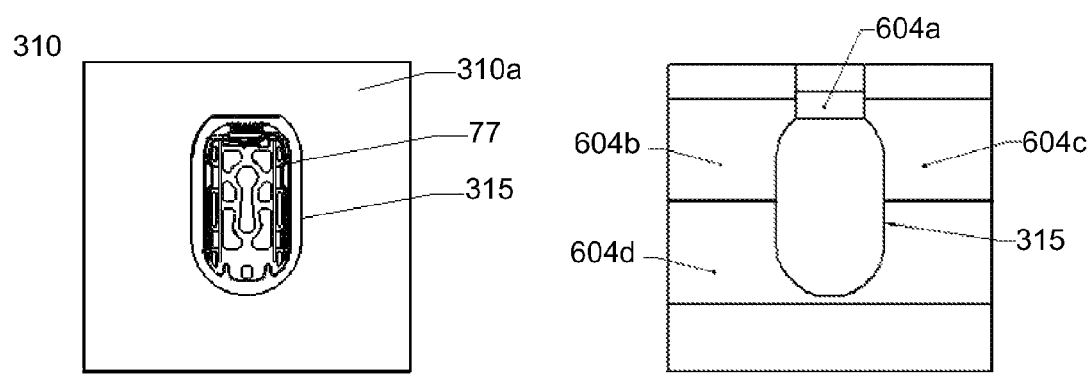
FIG. 12B shows the adhesive containing-securement element with release liner system thus removed, positioned about an on-body control unit mount.

An embodiment of a release liner system 600 having a plurality of release liners 604a, 604b, 604c, and 604d is shown in FIGS. 12A and 12B. FIG. 12A shows a release liner protective system 600 protecting a surface an adhesive surface 310b of securement element 310, e.g., adhesive 310b may be present on backing layer 310a, according to the subject invention. Front and back faces are shown in FIG. 12B, right and left figures respectively. Accordingly, left FIG. 12B shows securement element 310 with release liner system 600 thus removed and positioned about mounting unit 77, and more specifically the adhesive of securement element 310 is adhered to an adhesive patch (not shown) that retain mounting unit 77. Mounting unit 77 is positioned within control unit area 315.

Release liner system 600 may be used with any securement element, herein shown in FIGS. 12A and 12B as used with element 310 of FIG. 9B for exemplary purposes. Removable system 600 of peelable release layers 604 are adjacent one (adhesive) side 310b of element 310 and removable layer 602 is adjacent a second, opposite (backing) side 310a. Side 310b includes a plurality of release liners 604a, 604b, 604c and 604d, wherein more or less may be used.

In use, an on-body control unit may be first attached to a body part of a patient, e.g., using a first securement element in the form of an adhesive patch which, at one side, is attached to a body part and at a second side is attached to a mounting unit and control unit. To secure the control unit in place, a patient may hold second securement element 310 carrying release liner system 600 with one hand, e.g., with a right hand to apply to the left arm, and vice versa. A first release liner (e.g., release liner 604a) may be peeled away from securement element 310, e.g., using a tab or the like, and securement element 310, with the other release liners still in contact therewith, may be positioned about the control unit so that the hole of the securement element/release liner system is positioned around the control unit. Once positioned over the control unit, remaining release liners 604b, 604c . . . may be easily removed from securement element 310. Removable layer 602, if present, may be removed at any convenient time, e.g., before or after removal of release liner 604.

First and/or second on-body securement elements may be made from any suitable material where in many embodiments the material is selected for prolonged contact with skin with minimal skin irritation, as noted above. The material may be conformable to a patient's body part. Materials include but are not limited to those described herein and polyurethane; polyolefin, such as polyethylene and polypropylene; polyvinylchloride; ethylene vinyl acetate; woven fabrics; nonwoven fabrics; and the like, and may be perforated or nonperforated. In certain embodiments, the material may be perspiration-absorbing material. For example, elements may include a backing with an adhesive layer thereon. The backing may be fabricated from one or more of these materials.

As described, the subject invention, in accordance with various embodiments, may be used to secure any medical device to a body part and has been described primarily with reference to securing on-body analyte sensor control units to a body part. In such embodiments, any suitable analyte sensor may be employed, where exemplary analyte sensors are now described, where such description is in no way intended to limit the scope of the invention as it will be apparent that the subject invention is applicable to any analyte sensor and sensor system.

FIG. 13 shows an exemplary embodiment of an analyte sensor 42. Sensor 42 includes at least one working electrode 58 and a substrate 50. The sensor 42 may also include at least one counter electrode 60 (or counter/reference electrode) and/or at least one reference electrode 62 (see for example FIG. 18). The counter electrode 60 and/or reference electrode 62 may be formed on the substrate 50 or may be separate units. For example, the counter electrode and/or reference electrode may be formed on a second substrate which is also implantable in the patient or, for some embodiments of the sensors, the counter electrode and/or reference electrode may be placed on the skin of the patient with the working electrode or electrodes being implanted into the patient. The use of an on-the-skin counter and/or reference electrode with an implantable working electrode is described in, e.g., U.S. Pat. No. 5,593,852.

The working electrode or electrodes 58 are formed using conductive materials 52. The counter electrode 60 and/or reference electrode 62, as well as other optional portions of the sensor 42, such as a temperature probe 66 (see for example FIG. 18), may also be formed using conductive material 52. The conductive material 52 may be formed over a smooth surface of the substrate 50 or within channels 54 (see FIG. 14A) formed by, for example, embossing, indenting or otherwise creating a depression in the substrate 50.

A sensing layer 64 (see for example FIGS. 14A and 14B) may be provided proximate to or on at least one of the working electrodes 58 to facilitate the electrochemical detection of the analyte and the determination of its level in the sample fluid, particularly if the analyte cannot be electrolyzed at a desired rate and/or with a desired specificity on a bare electrode.

In addition to the electrodes 58, 60, 62 and the sensing layer 64, the sensor 42 may also include optional components such as one or more of the following: a temperature probe 66 (see for example FIGS. 16 and 18), a mass transport limiting layer 74, e.g., a matrix such as a membrane or the like, (see for example FIG. 19), a biocompatible layer 75 (see for example FIG. 19), and/or other optional components, as described below. Each of these optional items enhances the functioning of and/or results from sensor 42, as discussed below.

The substrate 50 may be formed using a variety of non-conducting materials, including, for example, polymeric or plastic materials and ceramic materials. Suitable materials for a particular sensor may be determined, at least in part, based on the desired use of the sensor and properties of the materials.

In addition to considerations regarding flexibility, it is often desirable that a sensor 42 should have a substrate 50 which is non-toxic. Substrate 50 may be one that is approved by one or more appropriate governmental agencies or private groups for in vivo use. Although substrate 50 in at least some embodiments has uniform dimensions along the entire length of the sensor, in other embodiments substrate 50 has a distal end 67 and a proximal end 65 with different widths 53, 55, respectively, as illustrated for example in FIG. 13.

At least one conductive trace 52 may be formed on the substrate for use in constructing a working electrode 58. In addition, other conductive traces 52 may be formed on the substrate 50 for use as electrodes (e.g., additional working electrodes, as well as counter, counter/reference, and/or reference electrodes) and other components, such as a temperature probe. The conductive traces 52 may extend most of the distance along a length 57 of the sensor 42 as illustrated for example in FIG. 13, although this is not necessary. The placement of the conductive traces 52 may depend on the particular configuration of the analyte monitoring system (e.g., the placement of control unit contacts and/or the sample chamber in relation to the sensor 42). For implantable sensors, particularly subcutaneously implantable sensors, the conductive traces may extend close to the tip of the sensor 42 to minimize the amount of the sensor that must be implanted.

The conductive traces may be formed using a conductive material 56 such as carbon (e.g., graphite), a conductive polymer, a metal or alloy (e.g., gold or gold alloy), or a metallic compound (e.g., ruthenium dioxide or titanium dioxide), and the like. Conductive traces 52 (and channels 54, if used) may be formed with relatively narrow widths. In embodiments with two or more conductive traces 52 on the same side of the substrate 50, the conductive traces 52 are separated by distances sufficient to prevent conduction between the conductive traces 52. The working electrode 58 and the counter electrode 60 (if a separate reference electrode is used) may be made using a conductive material 56, such as carbon.

Reference electrode 62 and/or counter/reference electrode may be formed using conductive material 56 that is a suitable reference material, for example silver/silver chloride or a non-leachable redox couple bound to a conductive material, for example, a carbon-bound redox couple.

The electrical contact 49 may be made using the same material as the conductive material 56 of conductive traces 52 or alternatively, may be made from a carbon or other non-metallic material, such as a conducting polymer.

A number of exemplary electrode configurations are described herein, however, it will be understood that other configurations may also be used. In certain embodiments, e.g., illustrated in FIG. 14A, the sensor 42 includes two working electrodes 58a, 58b and one counter electrode 60, which also functions as a reference electrode. In another embodiment, the sensor includes one working electrode 58a, one counter electrode 60, and one reference electrode 62, as shown for example in FIG. 14B. Each of these embodiments is illustrated with all of the electrodes formed on the same side of the substrate 50.

Figure 16:
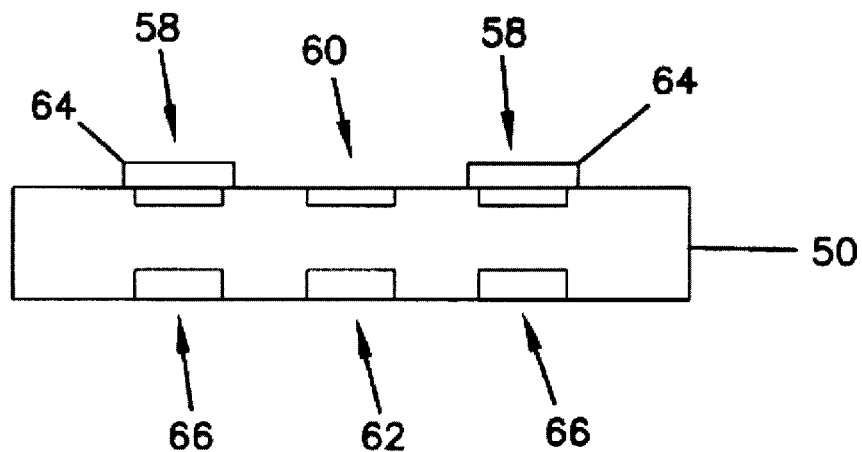
FIG. 16 is a cross-sectional view of another embodiment of an analyte sensor, according to one embodiment of the invention.
Figure 17:
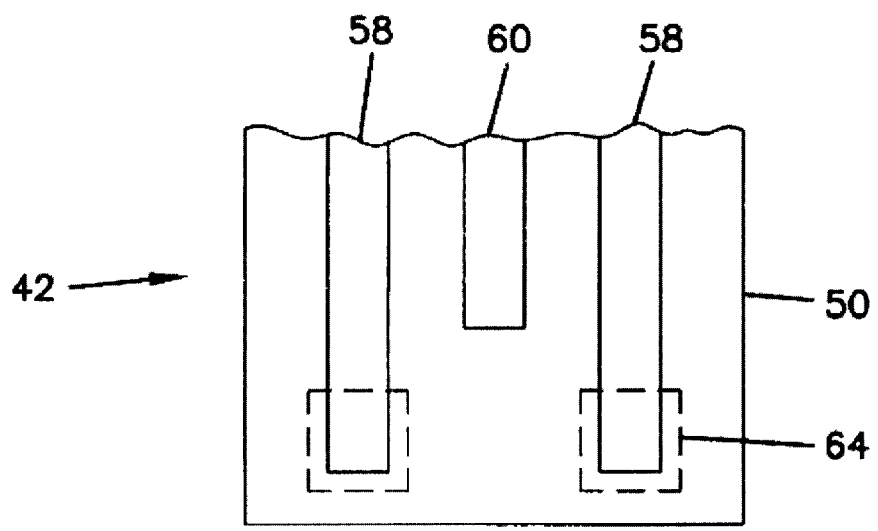
FIG. 17 is an expanded top view of a tip-portion of the analyte sensor of FIG. 16.
Figure 18:
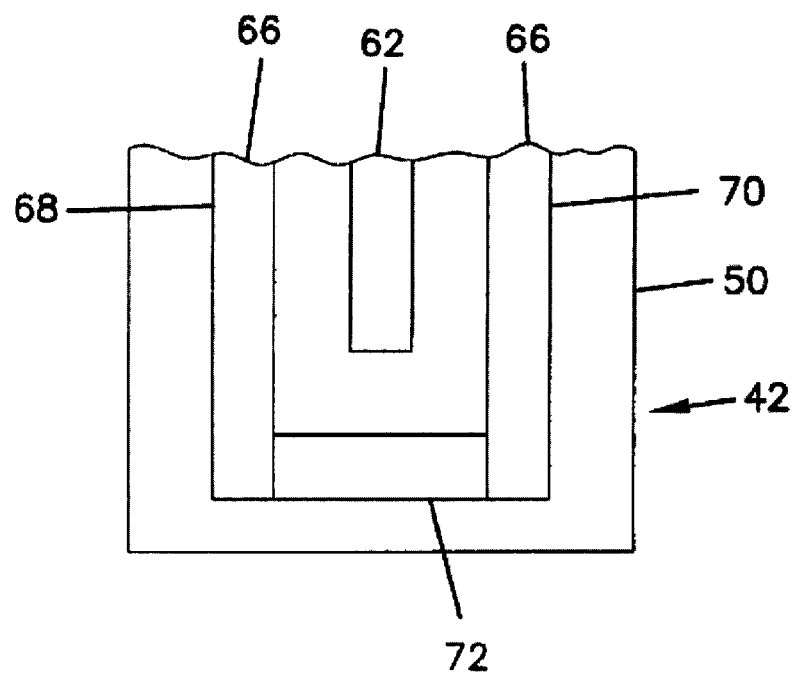
FIG. 18 is an expanded bottom view of a tip-portion of the analyte sensor of FIG. 16.

Alternatively, one or more of the electrodes may be formed on an opposing side of the substrate 50. In another embodiment, two working electrodes 58 and one counter electrode 60 are formed on one side of the substrate 50 and one reference electrode 62 and two temperature probes 66 are formed on an opposing side of the substrate 50, as illustrated in FIG. 16. The opposing sides of the tip of this embodiment of the sensor 42 are illustrated in FIGS. 17 and 18.

Some analytes, such as oxygen, may be directly electrooxidized or electroreduced on the working electrode 58. Other analytes, such as glucose and lactate, require the presence of at least one electron transfer agent and/or at least one catalyst to facilitate the electrooxidation or electroreduction of the analyte. Catalysts may also be used for those analytes, such as oxygen, that can be directly electrooxidized or electroreduced on the working electrode 58. For these analytes, each working electrode 58 has a sensing layer 64 formed proximate to or on a working surface of the working electrode 58. In many embodiments, the sensing layer 64 is formed near or on only a small portion of the working electrode 58, e.g., near a tip of sensor 42.

The sensing layer 64 includes one or more components designed to facilitate the electrolysis of the analyte. Sensing layer 64 may be formed as a solid composition of the desired components (e.g., an electron transfer agent and/or a catalyst). These components may be non-leachable from the sensor 42 and may be immobilized on the sensor 42. For example, the components may be immobilized on a working electrode 58. Alternatively, the components of the sensing layer 64 may be immobilized within or between one or more membranes or films disposed over the working electrode 58 or the components may be immobilized in a polymeric or sol-gel matrix. Examples of immobilized sensing layers are described in, e.g., U.S. Pat. Nos. 5,262,035; 5,264,104; 5,264,105; 5,320,725; 5,593,852; and 5,665,222; and PCT Patent Application No. US1998/002403 entitled "Electrochemical Analyte Sensors Using Thermostable Soybean Peroxidase", filed on Feb. 11, 1998, published as WO-1998/035053.

Sensors having multiple working electrodes 58a may also be used, e.g., and the signals therefrom may be averaged or measurements generated at these working electrodes 58a may be averaged. In addition, multiple readings at a single working electrode 58a or at multiple working electrodes may be averaged.

Figure 14A:
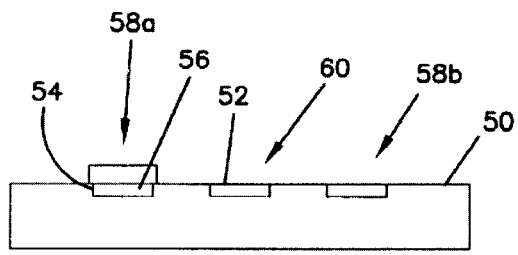
FIG. 14A is a cross-sectional view of the analyte sensor of FIG. 13.
Figure 14B:
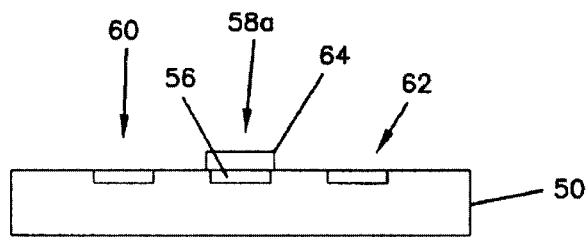
FIG. 14B is a cross-sectional view of another embodiment of an analyte sensor, according to one embodiment of the invention.
Figure 15A:
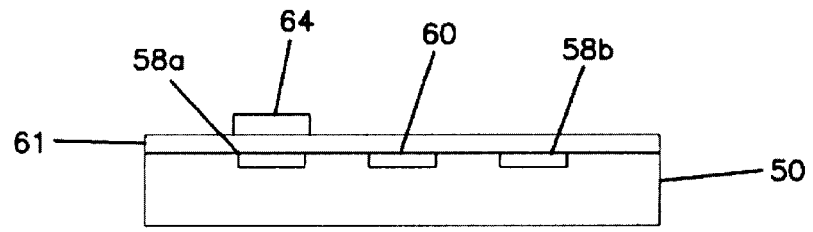
FIG. 15A is a cross-sectional view of another embodiment of an analyte sensor, according to one embodiment of the invention.
Figure 15B:
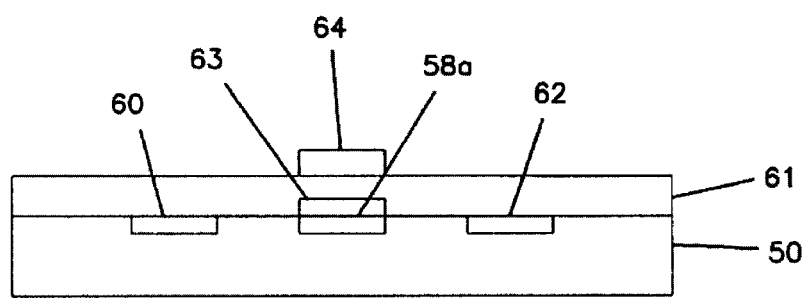
FIG. 15B is a cross-sectional view of a fourth embodiment of another embodiment of a sensor, according to one embodiment of the invention.

In many embodiments, sensing layer 64 contains one or more electron transfer agents in contact with the conductive material 56 of working electrode 58, as shown for example in FIGS. 14A and 14B. Useful electron transfer agents and methods for producing them are described in, e.g., U.S. Pat. Nos. 5,264,104; 5,356,786; 5,262,035; 5,320,725; 6,175,752; 6,329,161; and elsewhere. The sensing layer 64 may also include a catalyst which is capable of catalyzing a reaction of the analyte. The catalyst may also, in some embodiments, act as an electron transfer agent.

To electrolyze the analyte, a potential (versus a reference potential) is applied across the working and counter electrodes 58, 60. When a potential is applied between the working electrode 58 and the counter electrode 60, an electrical current will flow. Those skilled in the art will recognize that there are many different reactions that will achieve the same result; namely the electrolysis of an analyte or a compound whose level depends on the level of the analyte.

A variety of optional items may be included in a sensor. One optional item is a temperature probe 66 (see for example FIG. 18). One exemplary temperature probe 66 is formed using two probe leads 68, 70 connected to each other through a temperature-dependent element 72 that is formed using a material with a temperature-dependent characteristic. An example of a suitable temperature-dependent characteristic is the resistance of the temperature-dependent element 72. The temperature probe 66 can provide a temperature adjustment for the output from the working electrode 58 to offset the temperature dependence of the working electrode 58.

Figure 19:
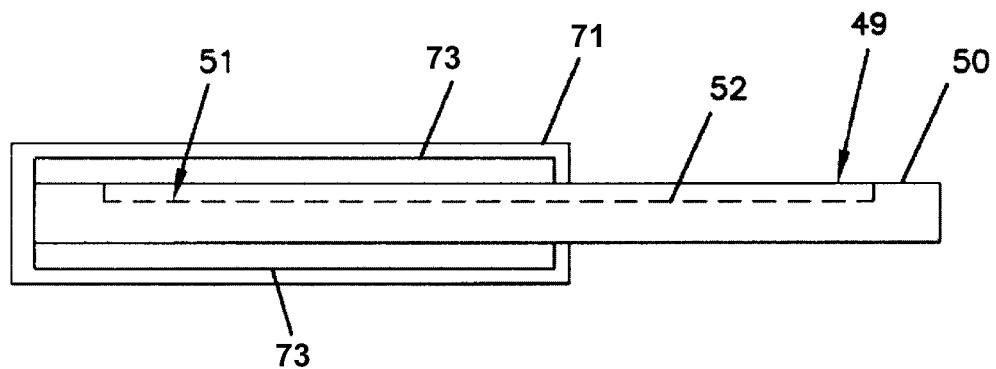
FIG. 19 is a side view of the analyte sensor of FIG. 13.

The sensors of the subject invention are biocompatible. Biocompatibility may be achieved in a number of different manners. For example, an optional biocompatible layer 73 may be formed over at least that portion of the sensor 42 which is inserted into the patient, as shown in FIG. 19.

An interferant-eliminating layer (not shown) may be included in the sensor 42. The interferant-eliminating layer may include ionic components, such as Nafion® or the like, incorporated into a polymeric matrix to reduce the permeability of the interferant-eliminating layer to ionic interferants having the same charge as the ionic components.

A mass transport limiting layer 71 may be included with the sensor to act as a diffusion-limiting barrier to reduce the rate of mass transport of the analyte, for example, glucose or lactate, into the region around the working electrodes 58. Exemplary layers that may be used are described for example, in U.S. Pat. No. 6,881,551, and elsewhere.

A sensor of the subject invention may be adapted to be a replaceable component in an in vivo analyte monitor, and particularly in an implantable analyte monitor. As described above, in many embodiments the sensor is capable of operation over a period of days or more, e.g., a period of operation may be at least about one day, e.g., at least about three days, e.g., at least about five days, e.g., at least about one week or more, e.g., one month or more. The sensor may then be removed and replaced with a new sensor.

The various embodiments of the present invention may also be employed to maintain a therapeutic agent delivery system on-body, e.g., an infusion device and/or infusion sets. Embodiments includes analyte monitoring systems used in sensor-based therapeutic agent (e.g., insulin) delivery systems, wherein the subject invention is included to secure one or more components thereof on a body part of a patient.

The system may provide a therapeutic agent to counteract the high or low level of an analyte in response to the signals from one or more sensors. Alternatively, the system may monitor the drug concentration to ensure that the drug remains within a desired therapeutic range. The system may include one or more (e.g., two or more) sensors, an on-skin sensor control unit and one or more on-body securement elements, a receiver/display unit, a data storage and controller module, and a drug administration system. In some cases, the receiver/display unit, data storage and controller module, and drug administration system may be integrated in a single unit. The sensor-based therapeutic agent delivery system may use data from the one or more sensors to provide necessary input for a control algorithm/mechanism in the data storage and controller module to adjust the administration of therapeutic agent. As an example, a glucose sensor may be used to control and adjust the administration of insulin.

Finally, kits for use in practicing the various embodiments of the subject invention are also provided. The subject kits may include one or more on-body securement elements as described herein. Embodiments may also include a sensor and/or a sensor control unit.

In addition to one or more of the above-described components, the subject kits may also include written instructions for using a sensor and/or on-body securement elements. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the Internet, are provided. An example of this embodiment is a kit that includes a web address where the instructions can be viewed and/or from which the instructions can be downloaded. As with the instructions, this means for obtaining the instructions is recorded on a suitable substrate.

In many embodiments of the subject kits, the components of the kit are packaged in a kit containment element to make a single, easily handled unit, where the kit containment element, e.g., box or analogous structure, may or may not be an airtight container, e.g., to further preserve the one or more sensors and additional reagents (e.g., control solutions), if present, until use.

In accordance with one embodiment of the present invention, mounting units with adhesive skin patches mated with control units and positioned on body surfaces (such as arm or abdomen) may be used in conjunction with second on-body securement elements retained substantially in its original position on the body surface for approximately 110 hours without substantial dislodgment. In the aforementioned embodiment, second on-body securement elements in the form of overbandages may be used. The overbandages include a casting layer, backing film, adhesive and release liner system, for example, as shown in to FIG. 12A, where a central through-hole is provided and sized to accommodate the control unit with a small clearance to facilitate application.

The overbandages may be designed to adhere only to the extended ring of the skin patch of the mounting unit and to provide increased adhesive area for skin adhesion. In this manner, the control units remained uncovered by the overbandages, reducing the likelihood of leaving adhesive residue on the control units. Moreover, this embodiment provides easier applications (with one hand and without line-of-sight) as compared to the other bandages. This may be achieved by the control units serving as lead-ins for positioning the overbandages, the tabs thereof exposing the "tack-in-place" spot of adhesive, and the easily removable release liner peel features.

In this manner, in one embodiment of the present invention, easy application and/or removal of overbandages for securing medical devices such as, for example, analyte sensor in combination with on-body securement elements is provided. Moreover, in accordance with the various embodiments of the present invention, there are provided devices and methods for maintaining a medical device on-body that provides, among others, ease of use, even in instances in which the medical device is to be maintained on a body part that is not within the direct line of site of the patient, and comfort. Furthermore, the subject invention in various embodiments provides a patient with a high degree of confidence that the medical device is securely maintained in position on a body part.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An on-body securement element for maintaining a medical device on a skin surface, the element comprising:
a non-adhesive backing having a first surface and a second surface;
an adhesive disposed on at least a portion of the first surface of the non-adhesive backing forming an adhesive portion and a non-adhesive portion on the first surface of the non-adhesive backing, the non-adhesive portion positionable over a medical device and sized and configured so that the medical device is not contacted with the adhesive portion when the non-adhesive portion is positioned over the medical device;
a release liner system comprising at least one removable release liner adjacent the adhesive; and
a removable casting layer adjacent the second surface of the non-adhesive backing;
wherein the non-adhesive portion comprises an opening, and wherein a transparent shield covers the opening.

2. The securement element of claim 1, wherein the adhesive portion is opaque.

3. The securement element of claim 1, wherein the non-adhesive portion comprises a pouch.

4. The securement element of claim 1, wherein the adhesive portion is configured for adherence to an adhesive patch on which the medical device is positioned.

5. The securement element of claim 1, wherein the release liner system comprises a plurality of removable release liners.

6. The securement element of claim 1, wherein the medical device includes one of a control unit, an RF receiver unit, a data monitoring device, an infusion device, or a remote control unit.

7. An on-body securement system for maintaining a continuous analyte monitoring system control unit on a skin surface, the system comprising:
a continuous analyte monitoring system control unit, the continuous analyte monitoring system control unit having a housing and a sensor extending from the housing;
a mounting unit having top surface, a bottom surface, an opening therethrough, a support structure located on the top surface, and a positioning structure located on the top surface, wherein the top surface is configured to receive the continuous analyte monitoring system control unit, the bottom surface is covered with an adhesive to adhere to the skin surface, the opening is configured to pass at least a portion of the sensor through the mounting unit and under the skin surface, the support structure is configured for holding the sensor in place and against conductive contacts of the continuous analyte monitoring system control unit, and the positioning structure is configured for facilitating positioning of the sensor; and
a securement element configured to be positionable over at least a portion of the mounting unit and the continuous analyte monitoring system control unit, wherein the securement element comprises:
a non-adhesive backing having a first surface and a second surface;
an adhesive disposed on at least a portion of the first surface of the non-adhesive backing forming an adhesive portion and a non-adhesive portion on the first surface of the non-adhesive backing, the non-adhesive portion positionable over the continuous analyte monitoring system control unit and sized and configured so that the continuous analyte monitoring system control unit is not contacted with the adhesive portion when the non-adhesive portion is positioned over the continuous analyte monitoring system control unit;
a release liner system comprising at least one removable release liner adjacent the adhesive; and a removable casting layer adjacent the second surface of the non-adhesive backing;
wherein the non-adhesive portion comprises an opening, and wherein a transparent shield covers the opening.

8. The system of claim 7, wherein the support structure and positioning structure are proximate to the opening.

9. The system of claim 8, wherein the positioning structure comprises an extension of material from the mounting unit that corresponds to a complementary structure of the sensor, wherein the sensor is positioned by aligning the positioning structure with the complementary structure of the sensor.

10. The system of claim 7, wherein the adhesive and the housing are water resistant or waterproof.

11. The system of claim 7, wherein the housing comprises a bottom surface, the bottom surface covered with a second adhesive, the second adhesive configured to fasten the continuous analyte monitoring system control unit to the top surface of the mounting unit.

12. The system of claim 7, wherein the mounting unit comprises a double-side adhesive strip.

13. The system of claim 7, wherein the transparent shield is configured to be positioned over the continuous analyte monitoring system control unit.

14. The system of claim 7, wherein the transparent shield is compressible.

15. The system of claim 7, wherein the release liner system comprises a plurality of removable release liners adjacent the adhesive covered surface.

* * * * *